US012601003B2

(12) United States Patent
Heron et al.

(10) Patent No.: US 12,601,003 B2
(45) Date of Patent: Apr. 14, 2026

(54) METHOD FOR SELECTING POLYNUCLEOTIDES BASED ON ENZYME INTERACTION DURATION

(71) Applicant: Oxford Nanopore Technologies PLC, Oxford (GB)

(72) Inventors: Andrew John Heron, Oxford (GB); Rebecca Victoria Bowen, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 226 days.

(21) Appl. No.: 16/960,006

(22) PCT Filed: Jan. 7, 2019

(86) PCT No.: PCT/GB2019/050029
§ 371 (c)(1),
(2) Date: Jul. 2, 2020

(87) PCT Pub. No.: WO2019/135091
PCT Pub. Date: Jul. 11, 2019

(65) Prior Publication Data
US 2021/0230665 A1 Jul. 29, 2021

(30) Foreign Application Priority Data
Jan. 5, 2018 (GB) ..................................... 1800187

(51) Int. Cl.
*C12Q 1/68* (2018.01)
*C12Q 1/6806* (2018.01)
*C12Q 1/686* (2018.01)
(52) U.S. Cl.
CPC ........... *C12Q 1/6806* (2013.01); *C12Q 1/686* (2013.01)
(58) Field of Classification Search
None
See application file for complete search history.

(56) References Cited

U.S. PATENT DOCUMENTS

| | | | | |
|---|---|---|---|---|
| 2004/0058378 A1* | 3/2004 | Kong | ................... | C12Q 1/6844 435/6.12 |
| 2011/0226623 A1* | 9/2011 | Timp | ................. | G01N 27/4146 204/543 |
| 2012/0322692 A1* | 12/2012 | Pham | ............... | G01N 33/54313 506/40 |
| 2014/0073513 A1* | 3/2014 | Drmanac | ............. | C12Q 1/6869 506/2 |

FOREIGN PATENT DOCUMENTS

| | | | | |
|---|---|---|---|---|
| WO | WO 2006/028508 A2 | 3/2006 | | |
| WO | WO 2010/086602 A1 | 8/2010 | | |
| WO | WO-2012129242 A2 * | 9/2012 | ............. | B01L 9/523 |
| WO | WO 2012/164270 A1 | 12/2012 | | |
| WO | WO-2013019759 A1 * | 2/2013 | .......... | C12Q 1/6806 |
| WO | WO 2013/057495 A2 | 4/2013 | | |
| WO | WO 2013/098561 A1 | 7/2013 | | |
| WO | WO 2013/098562 A2 | 7/2013 | | |
| WO | WO 2014/013259 A1 | 1/2014 | | |
| WO | WO 2014/013260 A1 | 1/2014 | | |
| WO | WO 2014/013262 A1 | 1/2014 | | |
| WO | WO-2014041337 A1 * | 3/2014 | ............. | C07H 21/04 |
| WO | WO 2014/135838 A1 | 9/2014 | | |
| WO | WO 2015/055981 A2 | 4/2015 | | |
| WO | WO-2015110813 A1 * | 7/2015 | ............... | C12N 9/93 |
| WO | WO-2015140535 A1 * | 9/2015 | .......... | C12Q 1/6869 |
| WO | WO 2015/150786 A1 | 10/2015 | | |
| WO | WO 2016/055777 A2 | 4/2016 | | |
| WO | WO 2016/059375 A1 | 4/2016 | | |
| WO | WO-2016059363 A1 * | 4/2016 | .......... | C12Q 1/6806 |
| WO | WO-2016059427 A1 * | 4/2016 | .......... | C12Q 1/6869 |
| WO | WO 2016/132123 A1 | 8/2016 | | |
| WO | WO 2017/203269 A1 | 11/2017 | | |

OTHER PUBLICATIONS

International Search Report and Written Opinion for Application No. PCT/GB2019/050029, mailed Mar. 1, 2019.
International Preliminary Report on Patentability for Application No. PCT/GB2019/050029, mailed Jul. 16, 2020.
Fuller et al., Real-time single-molecule electronic DNA sequencing by synthesis using polymer-tagged nucleotides on a nanopore array. Proc Natl Acad Sci U S A. May 10, 2016;113(19):5233-8. doi: 10.1073/pnas.1601782113. Epub Apr. 18, 2016.
Healy, Nanopore-based single-molecule DNA analysis. Nanomedicine (Lond). Aug. 2007;2(4):459-81. doi: 10.2217/17435889.2.4.459.
Kim et al., T7 DNA helicase: a molecular motor that processively and unidirectionally translocates along single-stranded DNA. J Mol Biol. Aug. 30, 2002;321(5):807-19. doi: 10.1016/s0022-2836(02)00733-7.
Kocalka et al., Rapid and efficient DNA strand cross-linking by click chemistry. Chembiochem. May 23, 2008;9(8):1280-5. doi: 10.1002/cbic.200800006.
Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::aid-anie2004>3.3.co;2-x.
Lin et al., Single-molecule imaging reveals the translocation and DNA looping dynamics of hepatitis C virus NS3 helicase. Protein Sci. Jul. 2017;26(7):1391-1403. doi: 10.1002/pro.3136. Epub Mar. 6, 2017.

(Continued)

*Primary Examiner* — Suryaprabha Chunduru
(74) *Attorney, Agent, or Firm* — Wolf, Greenfield & Sacks, P.C.

(57) ABSTRACT

A method for selecting polynucleotides, the method comprising: allowing a nucleic acid handling enzyme to move along multiple polynucleotides in a sample for a defined time period, wherein the enzyme is loaded onto each of the multiple polynucleotides and wherein one or more molecule of the enzyme moves along each of the multiple polynucleotides; and selecting polynucleotides based on whether or not the enzyme reaches the end of and/or unbinds from the polynucleotides in the defined time period.

24 Claims, 9 Drawing Sheets

Specification includes a Sequence Listing.

(56)　　　　　　　References Cited

OTHER PUBLICATIONS

Ramanagoudr-Bhojappa et al., Yeast Pif1 helicase exhibits a one-base-pair stepping mechanism for unwinding duplex DNA. J Biol Chem. May 31, 2013;288(22):16185-95. doi: 10.1074/jbc.M113. 470013. Epub Apr. 17, 2013.

Tolic-Nørrelykke et al., Diversity in the rates of transcript elongation by single RNA polymerase molecules. J Biol Chem. Jan. 30, 2004;279(5):3292-9. doi: 10.1074/jbc.M310290200. Epub Nov. 6, 2003.

* cited by examiner

Fig. 3
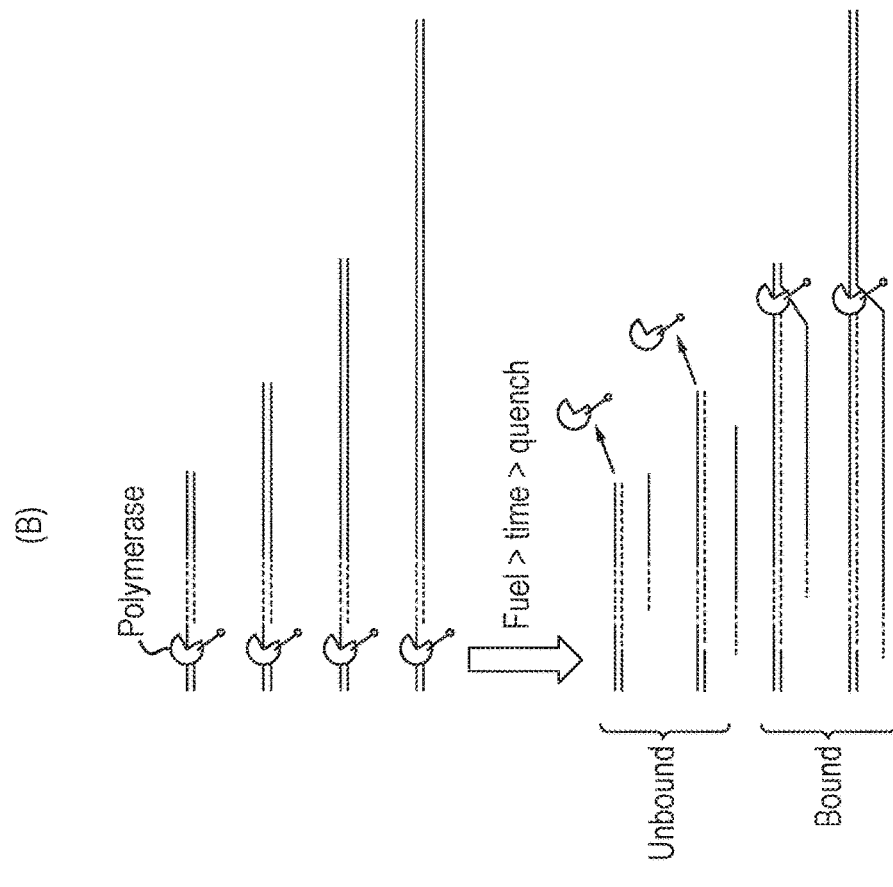
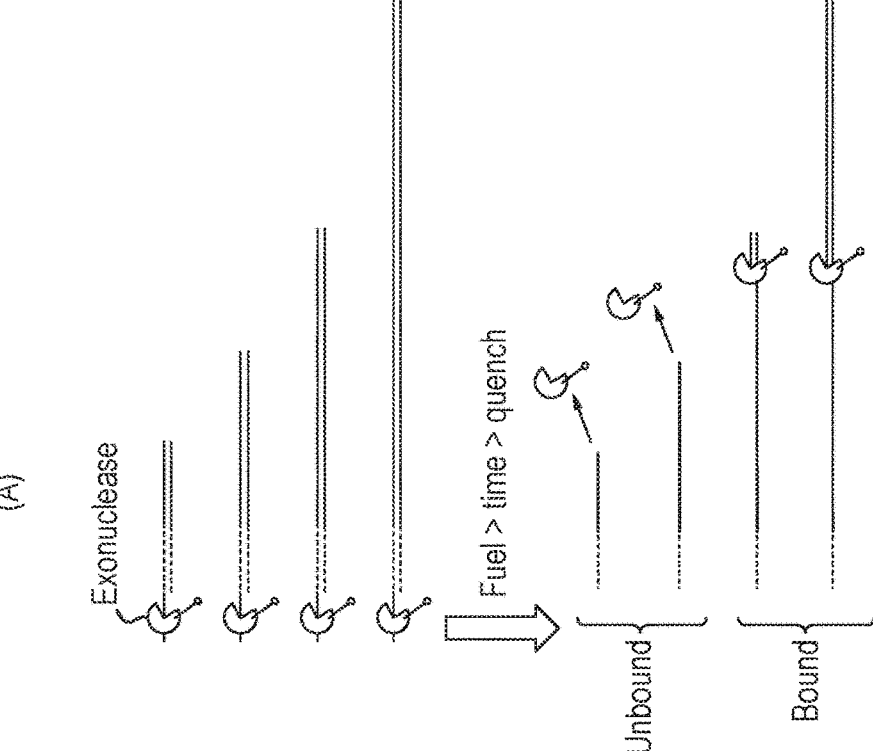

Fig. 5

Fig. 7
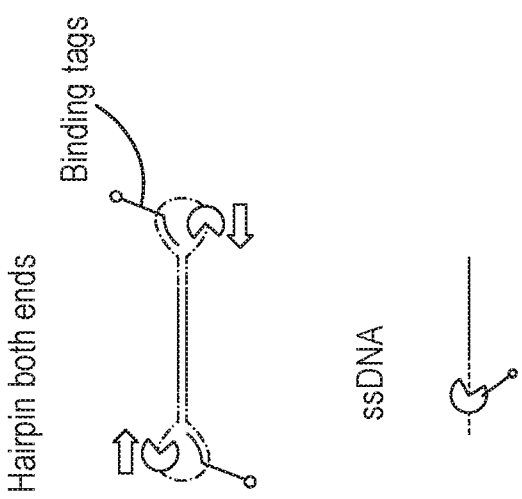
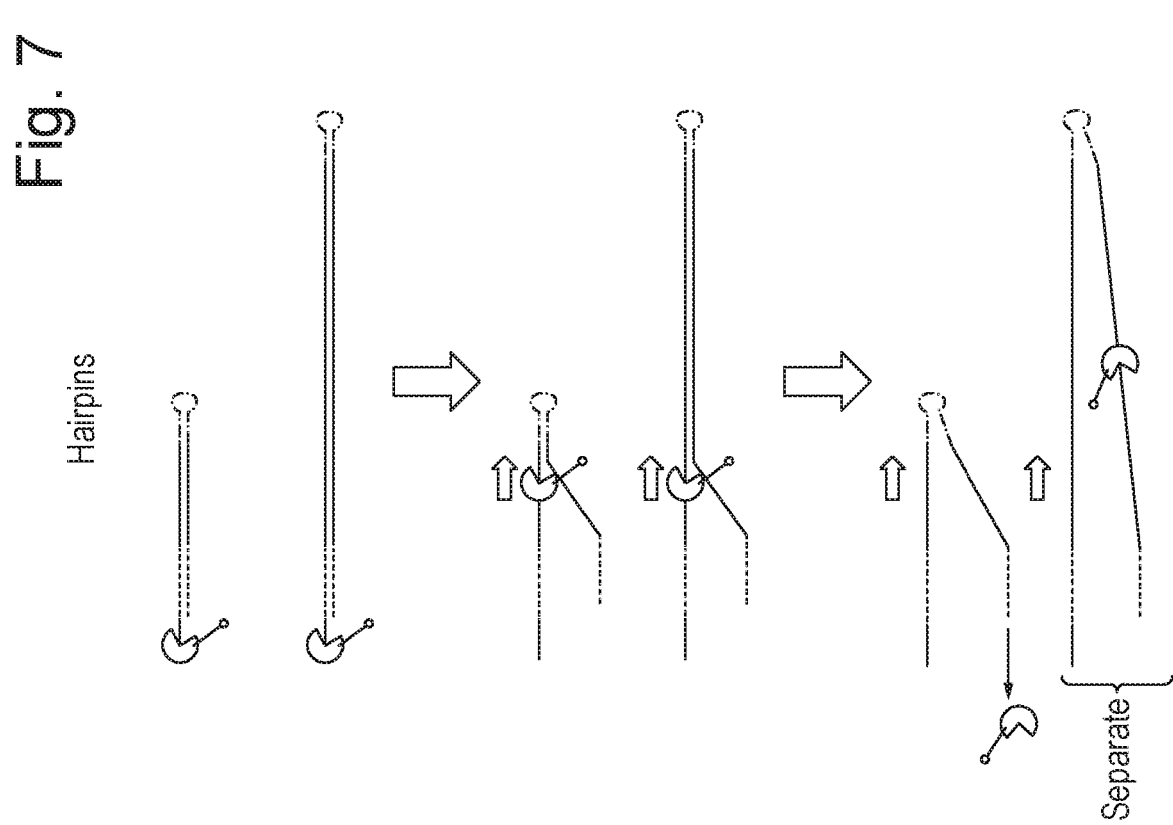

SEQUENCE LISTING

<160> NUMBER OF SEQ ID NOS: 6

<210> SEQ ID NO 1
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature -continued

```
<222> LOCATION: (1)..(1)
<223> OTHER INFORMATION: 5Phos

<400> SEQUENCE: 1
ggcgtctgct tgggtgttta accttttttt tttttaatgt acttcgttca gttacgtatt      60
gct                                                                    63

<210> SEQ ID NO 2
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5Phos

<400> SEQUENCE: 2
gcaatacgta actgaacgaa gtacatttt                                        29

<210> SEQ ID NO 3
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 3
ggttaaacac ccaagcagac gccagcaat                                        29

<210> SEQ ID NO 4
<211> LENGTH: 148
<212> TYPE: PRT
<213> ORGANISM: Artificial Sequence
<220> FEATURE:
<223> OTHER INFORMATION: Synthetic polypeptide

<400> SEQUENCE: 4

Met Gly Gly Ser Ala Trp Ser His Pro Gln Phe Glu Lys Gly Gly Gly
1               5                   10                  15

Ser Gly Gly Gly Ser Gly Gly Ser Ala Trp Ser His Pro Gln Phe Glu
            20                  25                  30

Lys Ser Gly Gly Gly Gly Gly Ser Asp Ser Glu Val Asn Gln Glu Ala
        35                  40                  45

Lys Pro Glu Val Lys Pro Glu Val Lys Pro Glu Thr His Ile Asn Leu
    50                  55                  60

Lys Val Ser Asp Gly Ser Ser Glu Ile Phe Phe Lys Ile Lys Lys Thr
65                  70                  75                  80

Thr Pro Leu Arg Arg Leu Met Glu Ala Phe Ala Lys Arg Gln Gly Lys
                85                  90                  95

Glu Met Asp Ser Leu Arg Phe Leu Tyr Asp Gly Ile Arg Ile Gln Ala
            100                 105                 110

Asp Gln Thr Pro Glu Asp Leu Asp Met Glu Asp Asn Asp Ile Ile Glu
        115                 120                 125

Ala His Arg Glu Gln Ile Gly Gly Ser Thr Ser Gly Ser Gly Glu Asn
    130                 135                 140

Leu Tyr Phe Gln
145

<210> SEQ ID NO 5
```

<211> LENGTH: 3561
<212> TYPE: DNA
<213> ORGANISM: Artificial Sequence
<220> FEATURE:
<223> OTHER INFORMATION: Synthetic polynucleotide

<400> SEQUENCE: 5
gccatcagat tgtgtttgtt agtcgctttt ttttttttgga attttttttt tggaatttttt      60 tttttgcgct aacaacctcc tgccgttttg cccgtgcata tcggtcacga acaaatctga     120
ttactaaaca cagtagcctg gatttgttct atcagtaatc gaccttattc ctaattaaat     180
agagcaaatc cccttattgg gggtaagaca tgaagatgcc agaaaaacat gacctgttgg     240
ccgccattct cgcggcaaag gaacaaggca tcggggcaat ccttgcgttt gcaatggcgt     300
accttcgcgg cagatataat ggcggtgcgt ttacaaaaac agtaatcgac gcaacgatgt     360
gcgccattat cgcctagttc attcgtgacc ttctcgactt cgccggacta agtagcaatc     420
tcgcttatat aacgagcgtg tttatcggct acatcggtac tgactcgatt ggttcgctta     480
tcaaacgctt cgctgctaaa aaagccggag tagaagatgg tagaaatcaa taatcaacgt     540
aaggcgttcc tcgatatgct ggcgtggtcg gagggaactg ataacggacg tcagaaaacc     600
agaaatcatg gttatgacgt cattgtaggc ggagagctat ttactgatta ctccgatcac     660
cctcgcaaac ttgtcacgct aaacccaaaa ctcaaatcaa caggcgccgg acgctaccag     720
cttctttccc gttggtggga tgcctaccgc aagcagcttg gcctgaaaga cttctctccg     780
aaaagtcagg acgctgtggc attgcagcag attaaggagc gtggcgcttt acctatgatt     840
gatcgtggta tatccgtca ggcaatcgac cgttgcagca atatctgggc ttcactgccg     900
ggcgctggtt atggtcagtt cgagcataag gctgacagcc tgattgcaaa attcaaagaa     960
gcgggcggaa cggtcagaga gattgatgta tgagcagagt caccgcgatt atctccgctc    1020
tggttatctg catcatcgtc tgcctgtcat gggctgttaa tcattaccgt gataacgcca    1080
ttacctacaa agcccagcgc gacaaaaatg ccagagaact gaagctggcg aacgcggcaa    1140
ttactgacat gcagatgcgt cagcgtgatg ttgctgcgct cgatgcaaaa tacacgaagg    1200
agttagctga tgctaaagct gaaaatgatg ctctgcgtga tgatgttgcc gctggtcgtc    1260
gtcggttgca catcaaagca gtctgtcagt cagtgcgtga agccaccacc gcctccggcg    1320
tggataatgc agcctccccc cgactggcag acaccgctga acgggattat ttcaccctca    1380
gagagaggct gatcactatg caaaaacaac tggaaggaac ccagaagtat attaatgagc    1440
agtgcagata gagttgccca tatcgatggg caactcatgc aattattgtg agcaatacac    1500
acgcgcttcc agcggagtat aaatgcctaa agtaataaaa ccgagcaatc catttacgaa    1560
tgtttgctgg gtttctgttt taacaacatt ttctgcgccg ccacaaattt tggctgcatc    1620
gacagttttc ttctgcccaa ttccagaaac gaagaaatga tgggtgatgg tttcctttgg    1680
tgctactgct gccggtttgt tttgaacagt aaacgtctgt tgagcacatc ctgtaataag    1740
cagggccagc gcagtagcga gtagcatttt tttcatggtg ttattcccga tgcttttttga    1800 agttcgcaga atcgtatgtg tagaaaatta aacaaaccct aaacaatgag ttgaaatttc    1860
atattgttaa tatttattaa tgtatgtcag gtgcgatgaa tcgtcattgt attcccggat    1920
taactatgtc cacagccctg acggggaact ctctgcggg agtgtccggg aataattaaa    1980
acgatgcaca cagggtttag cgcgtacacg tattgcatta tgccaacgcc ccggtgctga    2040 cacgaagaa accggacgtt atgatttagc gtggaaagat ttgtgtagtg ttctgaatgc    2100
tctcagtaaa tagtaatgaa ttatcaaagg tatagtaata tcttttatgt tcatggatat    2160

```
ttgtaaccca tcggaaaact cctgctttag caagattttc cctgtattgc tgaaatgtga    2220
tttctcttga tttcaaccta tcataggacg tttctataag atgcgtgttt cttgagaatt    2280
taacatttac aaccttttta agtccttta ttaacacggt gttatcgttt ctaacacga     2340 tgtgaatatt atctgtggct agatagtaaa tataatgtga gacgttgtga cgttttagtt    2400
cagaataaaa caattcacag tctaaatctt ttcgcacttg atcgaatatt tctttaaaaa    2460
tggcaacctg agccattggt aaaaccttcc atgtgatacg agggcgcgta gtttgcatta    2520
tcgtttttat cgtttcaatc tggtctgacc tccttgtgtt ttgttgatga tttatgtcaa    2580
atattaggaa tgttttcact taatagtatt ggttgcgtaa caaagtgcgg tcctgctggc    2640
attctggagg gaaatacaac cgacagatgt atgtaaggcc aacgtgctca aatcttcata    2700
cagaaagatt tgaagtaata tttaaccgc tagatgaaga gcaagcgcat ggagcgacaa      2760
aatgaataaa gaacaatctg ctgatgatcc ctccgtggat ctgattcgtg taaaaaatat    2820
gcttaatagc accatttcta tgagttaccc tgatgttgta attgcatgta tagaacataa    2880
ggtgtctctg gaagcattca gagcaattga ggcagcgttg gtgaagcacg ataataatat    2940
gaaggattat tccctggtgg ttgactgatc accataactg ctaatcattc aaactattta    3000
gtctgtgaca gagccaacac gcagtctgtc actgtcagga aagtggtaaa actgcaactc    3060
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc cttttgctc     3240 aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgtttta cgttaagttg atgcagatca attaatacga tacctgcgtc     3420
ataattgatt atttgacgtg gtttgatggc ctccacgcac gttgtgatat gtagatgata    3480
atcattatca ctttacgggt cctttccggt gaaaaaaaag gtaccaaaaa aaacatcgtc    3540
gtgagtagtg aaccgtaagc a                                              3561
```

<210> SEQ ID NO 6
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5'BNA-G
<220> FEATURE:
<221> NAME/KEY: misc_feature
<222> LOCATION: (2)..(2)
<223> OTHER INFORMATION: iBNA-G
<220> FEATURE:
<221> NAME/KEY: misc_feature
<222> LOCATION: (3)..(4)
<223> OTHER INFORMATION: iBNA-T
<220> FEATURE:
<221> NAME/KEY: misc_feature
<222> LOCATION: (5)..(5)
<223> OTHER INFORMATION: iBNA-A

<400> SEQUENCE: 6

```
ggttaaacac ccaagcagac gccagcaa                                        28
```

METHOD FOR SELECTING POLYNUCLEOTIDES BASED ON ENZYME INTERACTION DURATION

RELATED APPLICATIONS

This Application is a national stage filing under 35 U.S.C. § 371 of international application number PCT/GB2019/050029, filed Jan. 7, 2019, which claims the benefit of United Kingdom application number 1800187.5, filed Jan. 5, 2018, each of which is incorporated by reference in its entirety.

FIELD

The invention relates generally to methods of selecting polynucleotides. The invention also relates generally to methods of modifying, separating and/or characterising the selected polynucleotides.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 9, 2020, is named O036670097US00-SUBSEQ-KZM and is 7 kilobytes in size.

BACKGROUND

Selection of polynucleotides based on size is important for many applications, such as sequencing DNA and RNA. There is a need for rapid and cheap polynucleotide characterisation, identification, amplification and sequencing technologies across a wide range of applications. The length of the polynucleotide can aid in the identification of the polynucleotide. The length and integrity of the polynucleotide can also affect the success and rapidity of downstream identification, amplification or sequencing applications. Many high-throughput DNA sequencers require insert libraries of certain sizes for optimum performance. Other examples of applications for which polynucleotide size selection is important include ensuring correct PCR product formation, genotyping, DNA fingerprinting, gene profiling, and extracting a fragment of a defined size, for example following enzymatic digestion of a polynucleotide.

DNA of different sizes is conventionally detected by gel electrophoresis. Manual gel electrophoresis methods have many drawbacks and automated electrophoresis instruments that separate and select DNA of desired size ranges between 100 bp and 50 kb have been developed.

Functionalised, paramagnetic silica particles and polyethylene glycol (PEG) under different reaction conditions may be used for DNA size selection. Typically, these methods only allow the separation of DNA <1 kb in length. Size exclusion methods using a solid matrix can also be used, but again, these are typically for the removal of short <1 kb DNA fragments from 1000 kb+ fragments.

SUMMARY

The inventors have devised an enzyme based method of selecting polynucleotides in a sample comprising multiple polynucleotides. The inventors have recognised that the speed of movement of nucleic acid handling enzymes along the length of polynucleotides is consistent and does not depend on the length of the polynucleotide. The inventors have used this property of nucleic acid handling enzymes to devise methods in which movement of a nucleic acid handling enzyme is used to select polynucleotides of different lengths. The method involves selecting polynucleotides based on whether or not the enzyme remains bound to the polynucleotides after a predetermined time period, and/or on whether or not an enzyme reaches the end and/or falls off the polynucleotides. The method may be used to select polynucleotides of a desired length. The method may also be used to select undamaged polynucleotides and/or intact polynucleotides. Another use of the method is to select polynucleotides comprising adaptors at both ends from polynucleotides comprising an adapter at only one end and/or from non-adapted polynucleotides.

Accordingly, provided herein is a method for selecting polynucleotides, the method comprising:

(i) allowing a nucleic acid handling enzyme to move along multiple polynucleotides in a sample for a defined time period, wherein the enzyme is loaded onto each of the multiple polynucleotides and wherein one or more molecule of the enzyme moves along each of the multiple polynucleotides; and (ii) selecting polynucleotides based on whether or not the enzyme reaches the end of and/or unbinds from the polynucleotides in the defined time period.

The sample may, for example, comprise the products of a PCR reaction; genomic DNA; the products of a endonuclease digestion; or a DNA library.

The method may comprise one or more of the following:

selectively modifying polynucleotides of a desired length or selectively modifying polynucleotides undesired lengths;

selectively modifying undamaged polynucleotides or selectively modifying damaged polynucleotides;

selectively modifying intact polynucleotides or selectively modifying nicked polynucleotides;

separating polynucleotides of a desired length from other polynucleotides;

separating undamaged polynucleotides from damaged polynucleotides;

separating intact polynucleotides from nicked polynucleotides;

characterising polynucleotides of a desired length, undamaged polynucleotides and/or intact polynucleotides;

sequencing polynucleotides of a desired length, undamaged polynucleotides and/or intact polynucleotides;

removing primers or adapters from polynucleotides of a desired length, undamaged polynucleotides and/or intact polynucleotides; and genotyping, DNA fingerprinting or profiling using polynucleotides of a desired length, undamaged polynucleotides and/or intact polynucleotides.

Also provided are:

a method of characterising a polynucleotide, the method comprising:

(i) carrying out a method as described herein;

(ii) contacting a transmembrane pore with the selected polynucleotides;

(iii) applying a potential difference across the transmembrane pore; and (iv) taking one or more measurements which are indicative of one or more characteristics of a polynucleotide moving with respect to the transmembrane pore and thereby characterising the polynucleotide;

a polymer adapter which has bound thereto:

(a) a first nucleic acid handling enzyme;

(b) a second nucleic acid handling enzyme, which is bound such that its movement along the polymer is hindered until it is brought into contact with a trans-membrane pore, wherein the second nucleic acid handling enzyme does not hinder movement of the first nucleic acid handling enzyme; and optionally (c) a membrane anchor or pore anchor; and a kit for separating and/or selectively modifying poly-nucleotides comprising (a) an adapter comprising a polynucleotide and an end signal and/or (b) an adapter as described above; and comprising any one or more, including any combination, of the following compo-nents: an extraction medium; a nucleic acid handling enzyme; a nucleotide that provides energy for the enzyme, an enzyme cofactor and/or a coenzyme; a solution comprising fuel and/or cofactor for the nucleic acid handling enzyme; a wash solution, which does not contain fuel and/or cofactor for the nucleic acid han-dling enzyme; a site specific endonuclease; and/or a sequencing adapter.

DESCRIPTION OF THE FIGURES

It is to be understood that Figures are for the illustration purposes and are not intended to be limiting.

FIG. 3 shows examples of how selection criteria may be created using an exonuclease (A) or a polymerase (B). An exonuclease digests one strand of the polynucleotide. A polymerase will synthesise a complement, but otherwise can be used in a similar manner to a translocase. In the examples shown in the Figure, the exonuclease and the polynucleotide are tagged and the tag is used to separate short polynucle-otides from which the exonuclease or polymerase has dis-sociated from longer polynucleotides to which the exonu-clease or polymerase remains bound.

FIG. 4A shows displacement of a tag. FIG. 4B shows how the enzyme can alter the far end of the adapter (c. by unzipping or displacing components), such as its structure. The differences between ends that are altered versus intact ends can be exploited in subsequent attachment of adapters or components. For example, FIG. 4B illustrates how a structural change can be used to trap the complementary hybridization site on the end of the strand to prevent ligation of a sequencing adapter, so that sequencing adapters preferentially ligate to longer strands with intact ends. In this illustration there is no requirement to separate the oligonucleotides prior to sequencing-adapter attachments.

FIG. 5 shows an example of how the method may be implemented using enzymes in solution, rather than, for example, pre-loaded onto an adapter that is attached to the polynucleotides in the sample. In this method the use of adapters is optional, enzymes may instead bind naturally to the polynucleotides in the sample, either at the ends or to the middle of the strands. The enzyme is allowed to bind freely to the polynucleotides, optionally under conditions where the enzyme is free to move along the polynucleotides, e.g. in the presence of fuel such as ATP. Allowing the enzyme to bind in this manner will result in the eventual saturation of the strands by the enzyme. After enzyme has been allowed to bind to the polynucleotides, a defined time period is started by removing enzymes from solution and/or adding a large excess of capture strand to prevent additional molecules of enzyme from binding to the polynucleotides. The enzyme typically binds preferentially to the capture strand over the polynucleotides in the samples. At the end of the defined time period, enzyme movement is stopped, typically by quenching, and polynucleotides to which enzymes remain bound are separated from shorter polynucleotides to which enzymes are no longer bound.

FIG. 7 shows examples of polynucleotides that can be separated by the methods. The polynucleotide may comprise a hairpin adapter at one or both ends. Single stranded polynucleotides or double stranded polynucleotides may be separated by the method.

FIG. 8A shows an adapter that may be used in the separation method and then to facilitate characterisation of selected polynucleotides using a transmembrane pore. The adapter comprises a stalled nucleic acid handling enzyme and an un-stalled tagged enzyme. FIG. 8B shows how the adapter may be attached to polynucleotides prior to adding fuel to start movement of the un-stalled tagged enzyme along the polynucleotides. At the end of a defined time period, the movement of the tagged enzyme is stopped and longer polynucleotides to which the tagged enzyme is still bound are separated from shorter polynucleotides from which the tagged enzyme has been released. All of the polynucleotides retain an adapter having an enzyme stalled attached. Therefore, the polynucleotides of interest (which may be the longer polynucleotides or the shorter polynucleotides) are in a form that can immediately be sequenced using a transmembrane pore. The stalled enzyme serves to control the movement of the polynucleotides through a transmembrane pore. The stall is overcome when the stalled enzyme comes into contact with the transmembrane pore in the presence of fuel.

FIG. 9A compares the starting size distribution of the initial library (0 s incubation time) with the size distribution of the DNAs selected from the library after allowing the helicase to run for 240 seconds. FIG. 9B shows the distributions as binned histograms in separate panels. The histograms clearly show the reduction in strand counts for shorter strands in the 1-3 kilobases range, and a relative increase in strand count for strands greater than approximately 3 kilobases in length for the libraries with 120 s or 240 s incubation times.

DESCRIPTION OF THE SEQUENCE LISTING

Figure 1:
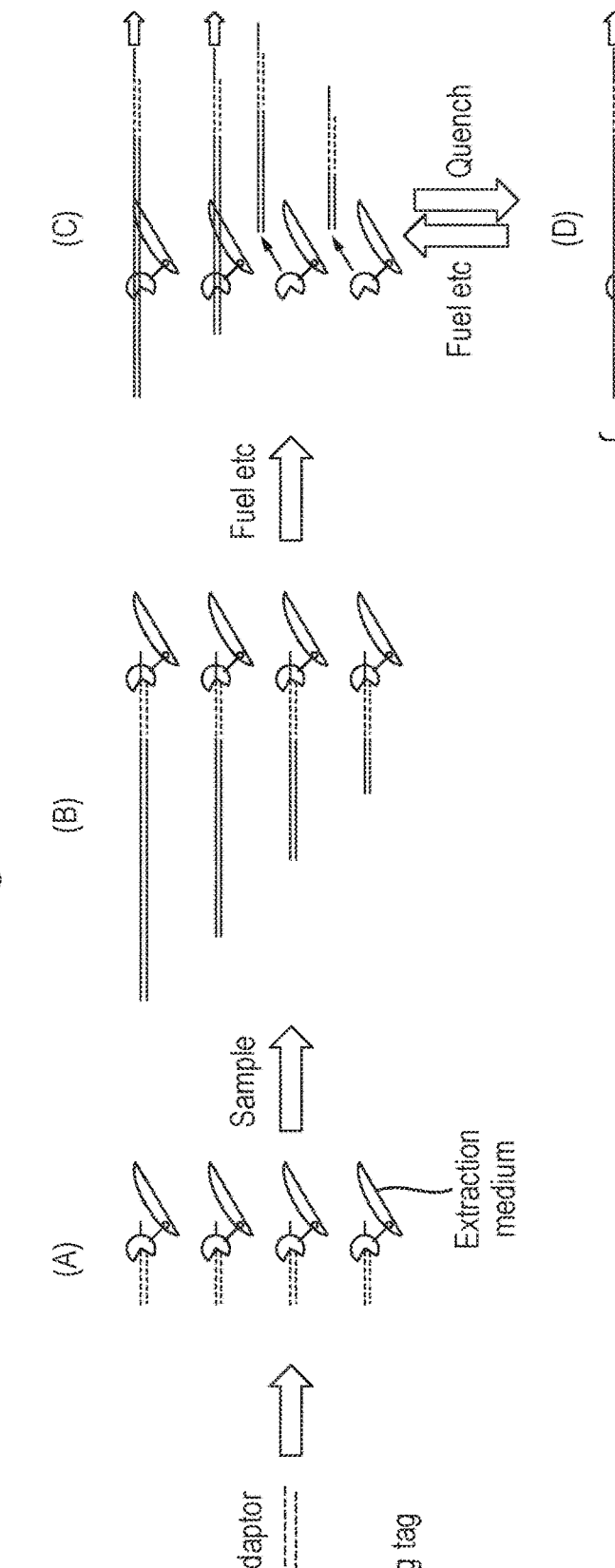
FIG. 1 shows a basic scheme where a nucleic acid handling enzyme is bound to a separating medium (e.g. beads), for example via a binding tag (e.g. a protein tag such as a his-tag or a strep-tag). (A) Enzyme adapter complexes bound to extraction media (e.g. beads). (B) Polynucleotides (e.g. double-stranded DNA) attached to adapters (e.g. by ligation). (C) Fuel and cofactor added and system run for desired period. The polynucleotides move relative to enzyme (the direction of the polynucleotides is indicated by arrows). The enzyme dissociates from a polynucleotide if it encounters a nick or gets to the end of a strand. If all enzymes are unbound the polynucleotide is capable of diffusing into solution. The released polynucleotides can be prevented from rebinding to free enzymes by various means. For example, trap oligonucleotides in solution can be designed to either bind and trap the enzymes, or bind and trap the free polynucleotide. Alternatively, the ends of the adapters can be designed such that enzymes cannot load (e.g. there are no free single-stranded sites). (D) When the system is quenched, longer polynucleotide strands remain bound to enzyme, and shorter strands or damaged strands have dissociated. Unbound polynucleotides (e.g. short strands or damaged strands) can be separated from bound polynucleotides by conventional means, for example by washing beads and optionally recovered. Bound polynucle-otides (e.g. longer strands) can be released and recovered in various ways. For example: the enzymes can be restarted by adding fuel and allowed to reach end of strands (step D back to step C); the enzymes can be unbound from the beads (e.g. denaturing enzyme, inhibiting the tag binding, cleaving tag/enzyme, etc.); or the enzymes can be unbound from the DNA (e.g. denaturing, high salt, un-closing the closed-complex, etc.). For size fraction selection, it is possible to recover any desired size fraction by looping between steps C>D>C>D . . . with loops of running for desired time>quenching>recovering elute from wash. For damaged strand selection, if after step D the long strands are eluted by re-adding fuel and running enzymes off the far ends of the polynucleotides, then any strands with damage that causes the enzyme to get stuck (e.g. abasic region, thymidine dimers, etc.) will remain bound to beads, and a can be separated from unbound strands which were released by enzymes reaching their ends. For nick selection, strands with nicks will elute with shorter strands as the enzyme falls off before making it to the end. Therefore, recovery after step D for long strands also selects for strands that contained no nicks (in at least one strand of a double stranded polynucle-otide if both ends were loaded with enzymes).
Figure 2:
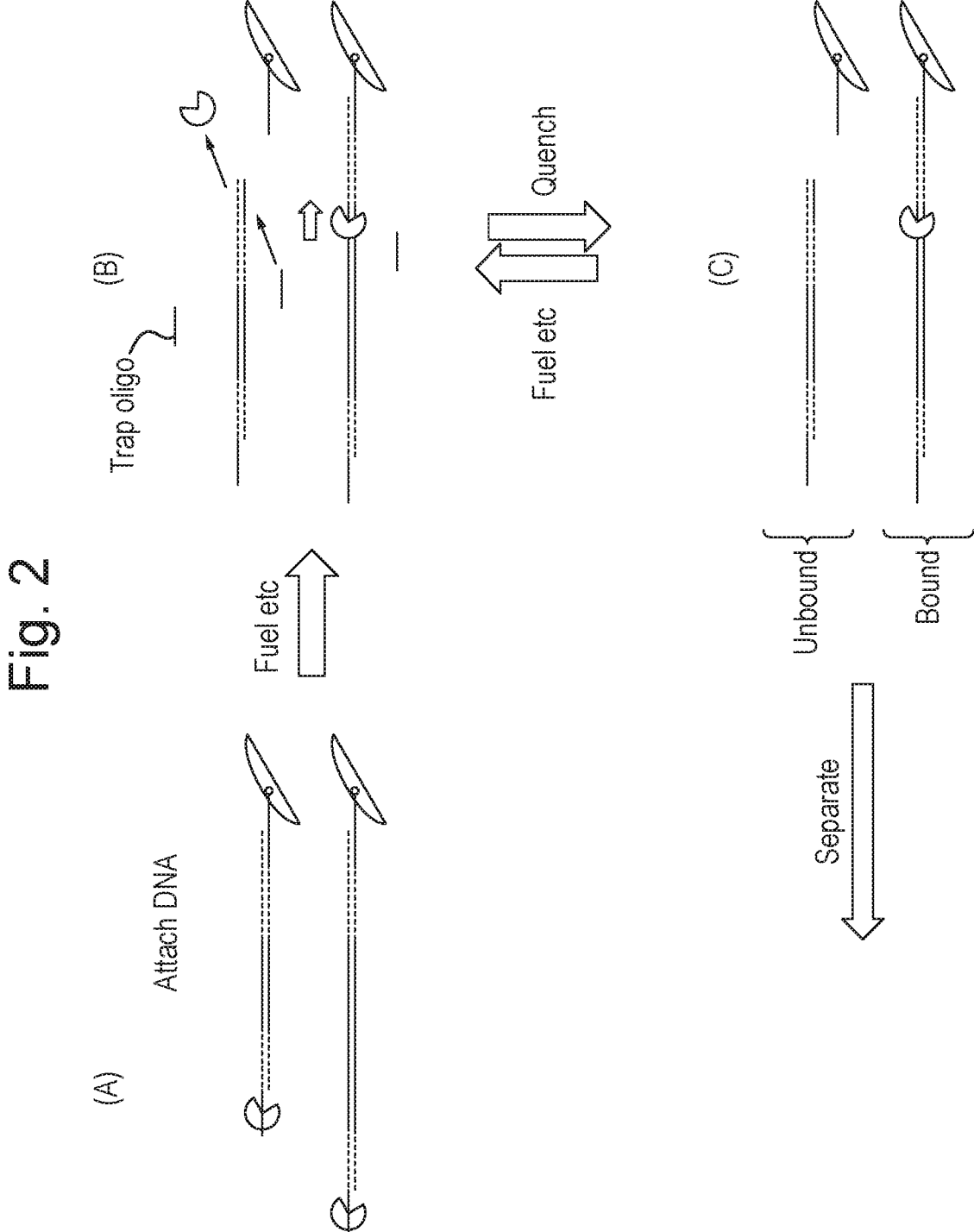
FIG. 2 shows a basic scheme where polynucleotides (e.g. double-stranded DNA) are bound to beads, for example via a binding tag, and an enzyme that reaches the far end of a polynucleotide can alter/displace the tag, and thus can be used to unbind the polynucleotide from the bead. For simplicity, this Figure shows an embodiment with two different adapters on a double stranded polynucleotide, one end with the enzyme and one end with the binding tag. (A) DNA complexes bound to extraction media via tag (e.g. a biotinylated oligonucleotide binding to streptavidin coated beads). (B) Fuel and cofactor added and system run for desired period. Enzyme moves along the polynucleotides (the direction of enzyme movement is indicated by arrows). Enzyme dissociates from a polynucleotide if it encounters a nick or gets to the end of a strand. If enzyme reaches the end of a polynucleotide, it displaces the binding tag, allowing the polynucleotide to dissociate from the bead. The released polynucleotide can be prevented from rebinding to the tag in various ways, for example by the addition of excess capture strands in solution, which bind to either the tag or the polynucleotide (Figure shows binding to polynucleotide). (C) When the system is quenched, long strands or strands where enzyme could not reach the end (e.g. due to nicks) remain bound to the beads via the tag, and short strands are unbound. Unbound polynucleotides (e.g. short strands) can be separated from bound nucleotides, for example by wash-ing the beads, and optionally recovered. Bound polynucle-otides (e.g. longer strands) can be released and recovered in various ways. For example: the enzymes can be restarted by adding fuel and allowed to reach end of strands (effectively looping back to step C); or the polynucleotides can be unbound from beads by other conventional means (e.g. unbinding tag, cleaving, elution conditions such as changing pH/temperature, etc.). For size-fraction selection, it is pos-sible to recover any desired size fraction by looping between steps B>C>B>C . . . with loops of running for desired time>quenching>recovering elute from wash. For damaged strand selection, if after step C the long strands are eluted by re-adding fuel and running enzymes off far end, then any strands with damage that prevents the enzyme reaching the end (e.g. abasic region, thymidine dimers, nicks, etc.) will remain bound to beads, and can be separated from unbound strands where enzymes reached the end.
Figure 4:
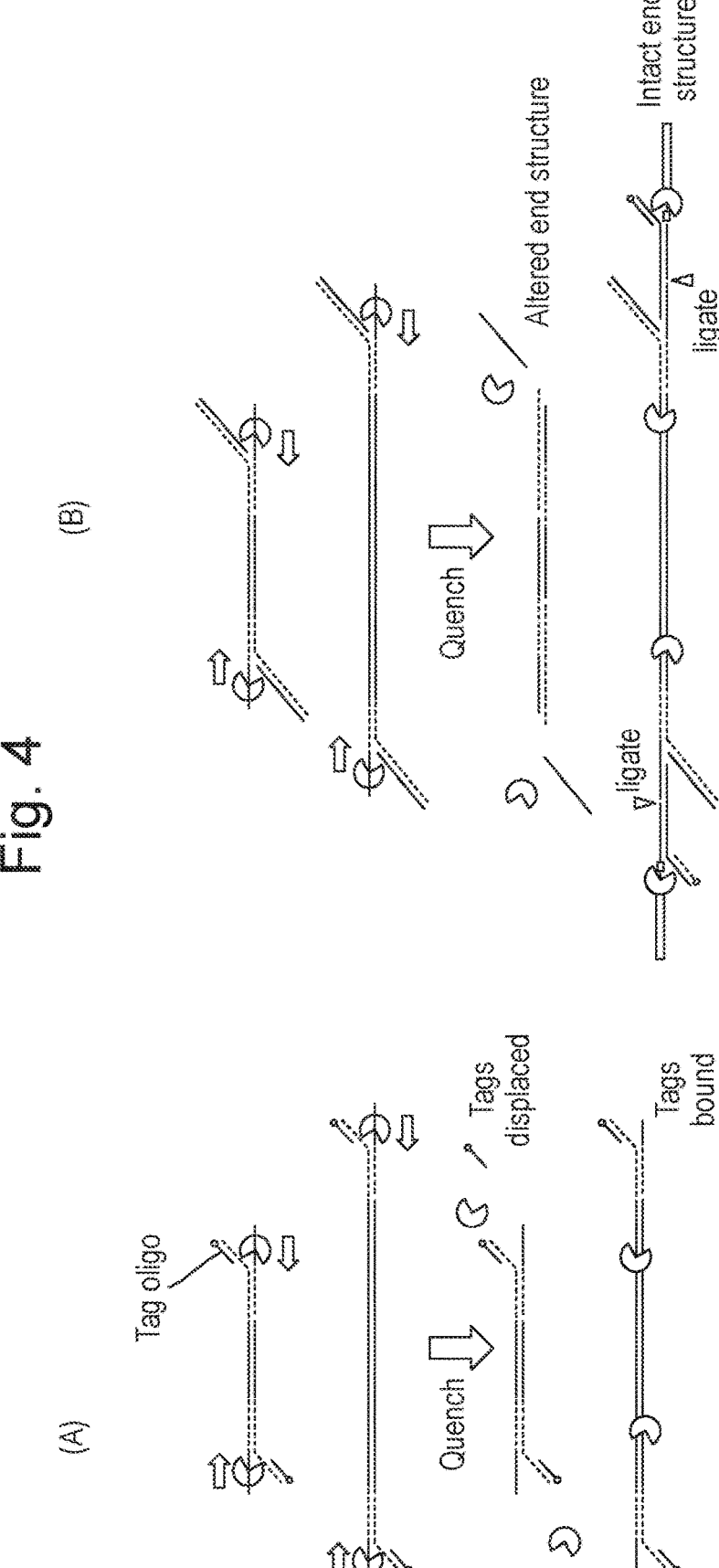
FIG. 4 shows examples of how a signal can be created if the enzyme reaches the far end of the strand.

SEQ ID NO: 1 is the nucleotide sequence of the top strand of the size selection adapter used in Examples 1 and 2.

SEQ ID NO: 2 is the nucleotide sequence of the bottom strand of the size selection adapter used in Examples 1 and 2.

SEQ ID NO: 3 is the nucleotide sequence of the blocker strand of the size selection adapter used in Example 1.

SEQ ID NO: 4 is the amino acid sequence of the strepSUMO tag attached to the DNA helicase used in Examples 1 and 2.

SEQ ID NO: 5 is the nucleotide sequence of the 3.6 kb DNA used in Example 1.

SEQ ID NO: 6 is the nucleotide sequence of the blocker strand of the size selection adapter used in Example 2.

It is to be understood that sequences are not intended to be limiting.

DETAILED DESCRIPTION

It is to be understood that different applications of the disclosed methods and products may be tailored to the specific needs in the art. It is also to be understood that the terminology used herein is for the purpose of describing particular embodiments of the methods and products only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, and reference to "a transmembrane pore" includes two or more pores and the like.

All publications, patents and patent applications cited herein, whether supra or infra, are hereby incorporated by reference in their entirety.

The present inventors have devised a method for selecting polynucleotides, the method comprising:

(i) allowing a nucleic acid handling enzyme to move along multiple polynucleotides in a sample for a defined time period, wherein the enzyme is loaded onto each of the multiple polynucleotides and wherein one or more molecule of the enzyme moves along each of the multiple polynucleotides; and (ii) selecting polynucleotides based on whether or not the enzyme reaches the end of and/or unbinds from the polynucleotides in the defined time period.

The method may further comprise separating the selected polynucleotides from the non-selected polynucleotides and/or selectively modifying the selected polynucleotides or the non-selected polynucleotides. Typically, the enzyme is loaded onto each of the multiple polynucleotides in the same manner.

Nucleic Acid Handling Enzyme

The method utilizes a nucleic acid handling enzyme to enable polynucleotides with different physical properties to be selectively modified and/or separated. The nucleic acid handling enzyme may be used as a marker to tag polynucleotides within a sample that meet the selection criteria, or alternatively to tag polynucleotides in the sample that do not meet the selection criteria. In another embodiment, the action of the nucleic acid handling enzyme alters a signal at the terminal end of the polynucleotide enabling that signal to be used to separate polynucleotides that meet the selection criteria from polynucleotides that do not meet the selection criteria. The signal at the terminal end of the polynucleotide may, for example, be a hidden signal that is exposed when the enzyme reaches the terminal end of the polynucleotide. Alternatively, the signal may be an exposed signal that is removed when the enzyme reaches the terminal end of the polynucleotide.

The nucleic acid handling enzyme may be any protein that is capable of binding to a polynucleotide and processing the polynucleotide. In processing the polynucleotide, the nucleic acid handling enzyme moves along the polynucleotide. The direction of movement of the enzyme is consistent. Consistent movement means that the enzyme moves from the 5' end to the 3' end of the polynucleotide or vice versa. The enzyme may modify the polynucleotide as it processes it. It is not essential that modification of the polynucleotide occurs. Therefore, the nucleic acid handling enzyme may be a modified enzyme that retains its ability to move along a polynucleotide.

The nucleic acid handling enzyme may be, for example, a translocase, a helicase, a polymerase or an exonuclease.

The nucleic acid handling enzyme may move along a single stranded polynucleotide, such as single stranded DNA or single stranded RNA, or may move along a double stranded polynucleotide such as double stranded DNA or a DNA/RNA hybrid. For example, helicases or translocases that act on either single stranded or double stranded DNA may be used.

The helicase may, for example, be a member of superfamily 1 or superfamily 2. The helicase is preferably a member of one of the following families: Pif1-like, Upf1-like, UvrD/Rep, Ski-like, Rad3/XPD, NS3/NPH-II, DEAD, DEAH/RHA, RecG-like, REcQ-like, T1R-like, Swi/Snf-like and Rig-I-like. The first three of those families are in superfamily 1 and the second ten families are in superfamily 2. The helicase is more preferably a member of one of the following subfamilies: RecD, Upf1 (RNA), PcrA, Rep, UvrD, Hel308, Mtr4 (RNA), XPD, NS3 (RNA), Mss116 (RNA), Prp43 (RNA), RecG, RecQ, T1R, RapA and Hef (RNA). The first five of those subfamilies are in superfamily 1 and the second eleven subfamilies are in superfamily 2. Members of the Upf1, Mtr4, NS3, Mss116, Prp43 and Hef subfamilies are RNA helicases. Members of the other subfamilies are DNA helicases.

The helicase may be a multimeric or oligomeric helicase. In other words, the helicase may need to form a multimer or an oligomer, such as a dimer, to function. The helicase is preferably monomeric. In other words, the helicase preferably does not need to form a multimer or an oligomer, such as a dimer, to function. For example, Hel308, RecD, TraI and XPD helicases are all monomeric helicases. These are discussed in more detail below. Methods for determining whether or not a helicase is oligomeric/multimeric or monomeric are known in the art. For instance, the kinetics of radiolabelled or fluorescently-labelled polynucleotide unwinding using the helicase can be examined. Alternatively, the helicase can be analysed using size exclusion chromatography.

Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers.

Particular examples of suitable helicases include Hel308, NS3, Dda, UvrD, Rep, PcrA, Pif1 and TraI. These helicases typically work on single stranded DNA. Examples of helicases that can move along both strands of a double stranded DNA include FtfK and hexameric enzyme complexes, or multisubunit complexes such as RecBCD.

The helicase may, for example, be any of the helicases, modified helicases or helicase constructs disclosed in WO 2013/057495, WO 2013/098562, WO2013098561, WO 2014/013260, WO 2014/013259, WO 2014/013262 and WO/2015/055981. The Hel308 helicase preferably comprises any one or more of the modifications disclosed in WO 2014/013260. The Dda helicase preferably comprises any one or more of the modifications disclosed in WO 2015/055981 and/or WO 2016/055777.

The nucleic acid handling enzyme may be a polymerase. A polymerase will typically synthesize a complementary polynucleotide strand as it moves along a polynucleotide. Otherwise, a polymerase may be used in a similar manner to a translocase. The polymerase may be a modified polymerase which retains its ability to move along a polynucleotide, but which does not synthesize a complementary strand. The polymerase may, for example, be PyroPhage® 3173 DNA Polymerase (which is commercially available from Lucigen® Corporation), SD Polymerase (commercially available from Bioron®) or variants thereof. The enzyme is preferably Phi29 DNA polymerase or a variant thereof.

Synthesis of a complementary strand may be advantageous in that it increases the amount of polynucleotide. Increasing the amount of polynucleotide may improve sensitivity of any subsequent assay using the polynucleotide selected by the method. Where the polynucleotide contains modified bases, the polymerase may be used to synthesize a complementary strand that contains normal bases, which can also be advantageous for subsequent assays using the polynucleotide.

Using a polymerase may have the advantage that it can be used to distinguish a damaged polynucleotide from an undamaged polynucleotide. For example, the polymerase may be unable to pass through an abasic nucleotide in DNA or through thymidine dimers. Accordingly, a method using a polymerase may be used to separate damaged polynucleotides from undamaged polynucleotides.

The nucleic acid handling enzyme may be an exonuclease. An exonuclease typically digest the polynucleotide as it moves along it. The exonuclease typically cleaves one strand of a double stranded polynucleotide to form individual nucleotides or shorter chains of nucleotides, such as di- or tri-nucleotides. Where an exonuclease is used, the polynucleotides which are ultimately selected are the undigested strands of double stranded polynucleotide, or polynucleotides in which one of the strands is partially digested and the other strand is intact. Any exonuclease enzyme may be used in the method. Preferred enzymes for use in the method include exonuclease III enzyme from *E. coli*, exonuclease I from *E. coli*, bacteriophage lambda exonuclease and enzymes derived from exonuclease III enzyme from *E. coli*, exonuclease I from *E. coli*, bacteriophage lambda exonuclease. An enzyme derived from one of these exonucleases preferably comprises the domains responsible for binding to the nucleic acid and for digesting the nucleic acid (catalytic domain).

The nucleic acid handling enzyme is preferably one that is able to process long polynucleotide strands without unbinding from the polynucleotide. Typically, the nucleic acid handling enzyme is capable of moving along a polynucleotide strand of from 500 nucleotide base pairs up to 250 million nucleotide base pairs, such as from 1,000, 2,000, 5,000, 10,000, 50,000 or 100,000 nucleotide base pairs up to 200 million, 100 million, 10 million or 1 million nucleotide base pairs.

The enzyme may be modified or unmodified. The enzyme may be modified to form a closed-complex. A closed-complex is an enzyme in which the polynucleotide binding site is modified such that the enzyme is closed around the polynucleotide in such a way that the enzyme does not fall off the polynucleotide other than when it reaches the end of the polynucleotide. Examples of suitable closed-complex enzymes and methods for modifying enzymes to produce closed complexes are disclosed in, for example, WO 2014/013260 and WO 2015/055981.

Where the nucleic acid handling enzyme is an unmodified polymerase, the enzyme is typically capable of moving along a polynucleotide of up to 30 kb. The distance of movement may be increased by modifying the polymerase to close an opening from which the polynucleotide is able to unbind when the enzyme is part way along the polynucleotide. For such a modified polymerase, the longer polynucleotide lengths specified above may be processed by the polymerase.

During step (i) of the method, one molecule of the enzyme may move along each of the multiple polynucleotides. In alternative embodiments, multiple molecules of the enzyme may move along each of the multiple polynucleotides. The number of molecules of the enzyme moving along each of the multiple polynucleotide will depend on the method of loading the enzyme onto the polynucleotides.

Where multiple molecules of the enzyme move along the multiple polynucleotides, the exact number of molecules is not important. For example, at least one, preferably at least 2, 3, 4, 5, 6, 7, 8, 9 or 10 molecules of the enzyme may move along a polynucleotide. All that is required for a method which uses multiple molecules of an enzyme on each of the multiple polynucleotides is that at the end of the defined time period, polynucleotides to which one or more molecule of the enzyme remains bound can be separated from polynucleotides to which no molecules of the enzyme remain bound, or alternatively that polynucleotides which have had at least one molecule of the enzyme pass the terminal end can be separated from polynucleotides where none of the molecules of bound enzyme have reached the terminal end. In these methods, the enzyme is added in solution either prior to step (i) or to initiate the defined time period in step (i). Binding enzymes from solution has the advantage that it simplifies sample preparation. Where the enzyme is in solution, binding of the enzyme to the start of the polynucleotide can occur freely. Binding of the enzyme in solution to the initial polynucleotides may be stopped or prevented by sequestering free enzyme in solution, such as, for example, by adding a capture polynucleotide (capture strand) or other capture molecule, such as heparin. A capture polynucleotide or molecule is preferentially bound by the free enzyme, due to its higher relative affinity for the free enzyme, than the polynucleotide that is being characterised/the target polynucleotide. The higher affinity can be achieved by providing a the capture polynucleotide or molecule at a higher concentration than the polynucleotide being characterised.

A capture strand is typically a short strand of DNA or RNA to which helicase binds. The capture strand may have a length of from about 15 nucleotides to about 40 nucleotides, such as about 20, about 25 or about 30 nucleotides. The capture strand is typically added at a high concentration in solution to promote binding of helicase in solution to the capture strand in preference to the polynucleotides being separated. The skilled person will readily be able to identify a suitable concentration of capture strand. The concentration may, for example, be from about 10 nM to about 1M, such as from about 50 nM to about 500 mM or about 1 mM to 100 mM.

Figure 5:
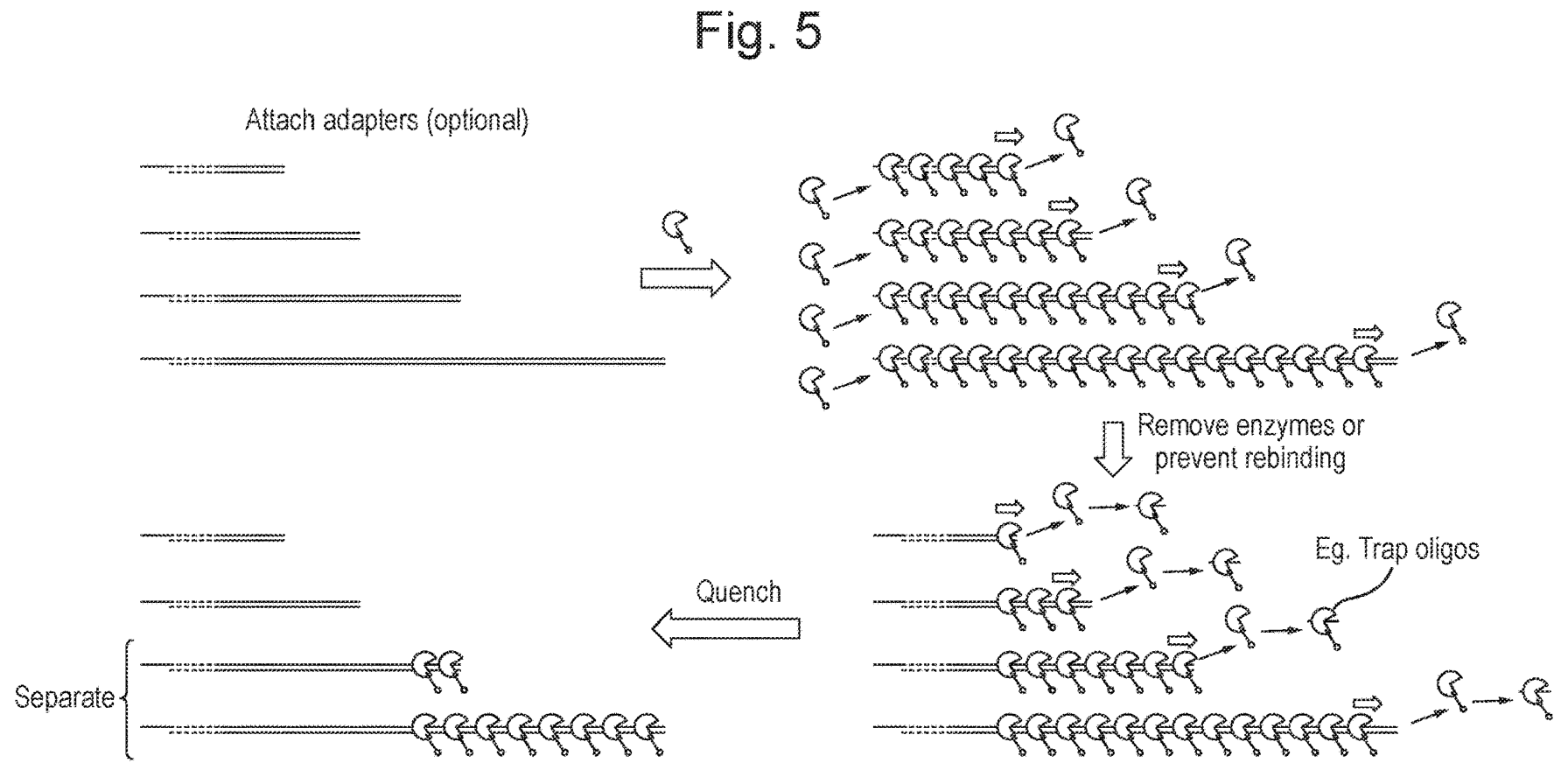
Figure 6:
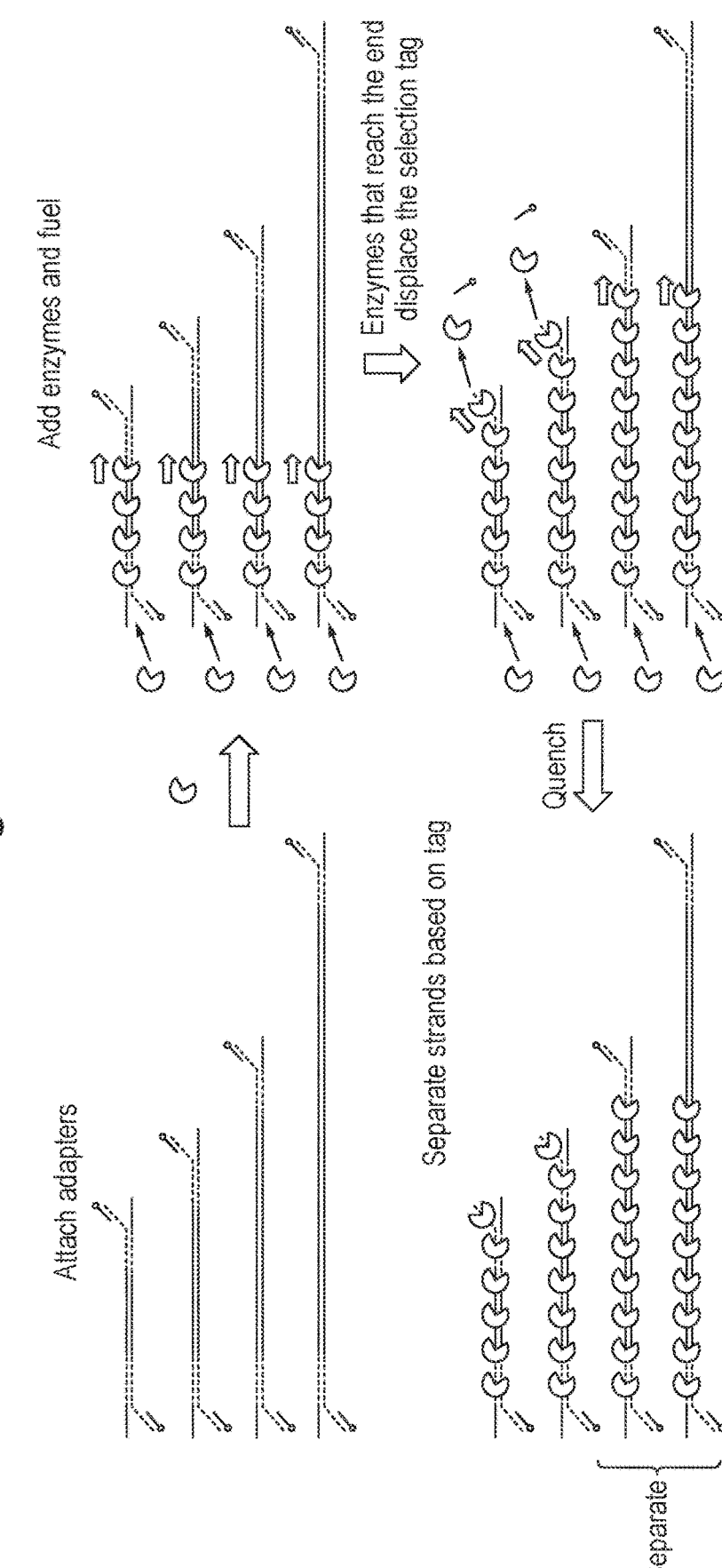
FIG. 6 shows a further example of how the method may be implemented using enzymes in solution. In this method tagged adapters are used. A defined time period is started by contacting the polynucleotides with the enzyme in solution containing the cofactors and fuel necessary for the enzyme to move along the polynucleotides. In this example, the enzymes are only able to load onto the ends of the polynucleotides in the sample via the attached adapter. For clarity the Figure only shows enzymes loading onto the single-stranded overhang of the left adapter and running along the top strand of the polynucleotides. Enzymes that reach the end of the polynucleotides displace a selection tag in the adapter at the end of the polynucleotide. At the end of the time period enzyme movement is stopped and polynucleotides which retain the selection tag are separated from shorter polynucleotides from which the selection tag has been displaced.
Figure 8:
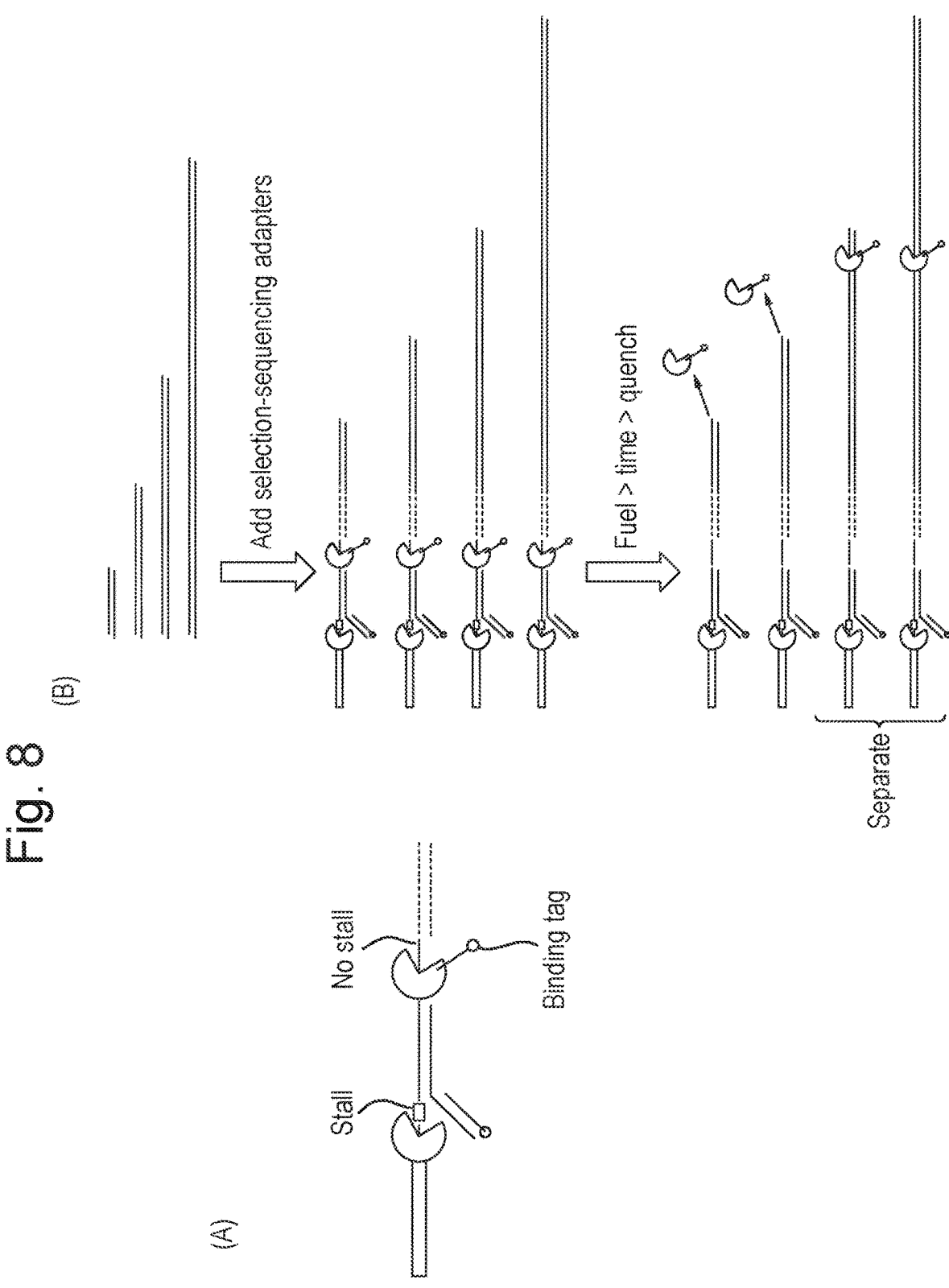
FIG. 8 shows one particular example of how the method may be used to select and prepare polynucleotides for characterisation using a transmembrane pore using a dual purpose adapter that comprises (1) a tagged enzyme for size selection; and (2) a leader sequence, a stalled enzyme and a membrane tether for nanopore sequencing.

FIGS. 5 and 6 show schematic examples of how the method can utilise enzymes in solution. Where the enzyme is in solution, more enzymes will typically continue to bind. Therefore, the selection is not based on the use of a single enzyme. Selection can be based on enzyme reaching end to create or destroy a signal (FIG. 6). Selection can be based on tagged enzymes (FIG. 5). For simplicity, binding from only one end of the strand is shown in FIGS. 5 and 6.

Loading Enzyme onto Polynucleotide

In one embodiment, the method comprises an initial step of binding the enzyme to the multiple polynucleotides. Thus, at the start of step (i) one or more molecules of the enzyme may be bound to each of the multiple polynucleotides. Only one molecule of enzyme may be bound to each of the multiple polynucleotides at the start of step (i) or multiple molecules of the enzyme may be bound to each of the multiple polynucleotides at the start of step (i).

Where only one molecule of enzyme is bound to each of the multiple polynucleotides, the enzyme is typically prebound to an adapter. The initial step of binding the enzyme to the multiple polynucleotides may therefore comprise attaching an adapter having an enzyme bound thereto to one or both ends of the multiple polynucleotides.

Where multiple molecules of the enzyme are bound to each of the multiple polynucleotides prior to step (i), the enzymes are added to the polynucleotides in solution during the initial step of binding the enzyme to the multiple polynucleotides. In this embodiment, adapters may also be attached to the polynucleotides prior to addition of the enzyme in solution. The use of an adapter is not essential in this embodiment. Many enzymes, helicases in particular, can bind to genomic DNA with a range of available ends. Typically, in an embodiment which uses no end adapters, the nucleic acid handling enzyme comprises a selection tag, e.g. a selection tag is bound to the enzyme. Where an adapter is used, the adapter may contain, for example, a poly T loading site for a helicase, or for two or more helicases. The adapter may be designed for enzymes that move in the 5'-3' or 3'-5' direction as required.

In an alternative embodiment, at the start of step (i) there may be no molecules of the enzyme bound to any of the multiple polynucleotides. In this embodiment, the defined time period is started by adding the enzyme to the sample in solution. Any fuel, coenzymes or cofactors necessary for movement of the enzyme may be added prior to, or together with the enzyme.

Sample

The sample may be any suitable sample comprising polynucleotides. The polynucleotides may, for example, comprise the products of a PCR reaction, genomic DNA, the products of a endonuclease digestion and/or a DNA library.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus.

The sample is preferably a fluid sample. The sample typically comprises a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs.

Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to carrying out the method, for example by centrifugation or by passage through a membrane that filters out unwanted molecules or cells, such as red blood cells. The method may be performed on the sample immediately upon being taken. The sample may also be typically stored prior to the method, preferably below −70° C.

The sample may comprise genomic DNA. The genomic DNA may be fragmented. The DNA may be fragmented by any suitable method. For example, methods of fragmenting DNA are known in the art, Such methods may use a transposase, such as a MuA transposase. Preferably the genomic DNA is not fragmented.

The polynucleotides may be unmodified. Adapters may be added to one or both ends of the polynucleotides in the sample. Suitable adapters are defined below.

In one embodiment, a hairpin adapter may be added to one or both ends of the polynucleotides. Where a hairpin adapter is added to both ends of the polynucleotides, an enzyme is preferably prebound to the adapters. In this embodiment, the hairpins will typically prevent the enzyme from falling off the ends of the polynucleotides. Therefore, the adapters preferably comprise a signal that is removed or activated when an enzyme moves from the adapter at one end of the polynucleotide to the adapter at the other end of the polynucleotide. Examples of embodiments using hairpin adapters are shown in FIG. 7.

Multiple Polynucleotides

The disclosed method is used to select polynucleotides from a sample comprising multiple polynucleotides. The term "multiple" is used herein to mean two or more different polynucleotides, such as from about at least 2, at least 3 or at least 4 to about 100,000 or more, for example from about at least 5 to about 50,000 or more, about at least 10 to about 10,000 or more polynucleotides.

In certain exemplary embodiments, the sample may comprise at least about 20, at least about 50, at least about 100, at least about 500 or at least about 1,000 different polynucleotides.

The polynucleotides separated by the method may be, for example, DNA, RNA and/or DNA/RNA hybrids. The DNA may be double stranded or single stranded. The sample may comprise different polynucleotides of the same type, such as, for example, different DNAs, different RNAs or different RNA/DNA hybrids. The sample may comprise multiple types of polynucleotide such as any two or more of DNA, RNA and DNA/RNA hybrids.

The polynucleotide can be in any suitable form. Adapters may be added to one or both ends of the polynucleotides. The adapters may, for example, be used to ensure equal loading of the enzyme onto different polynucleotides within a sample and/or to ensure that the polynucleotides in the sample are in the same form. Any suitable adapter design may be used. For example the adapters may be designed for single or double-ended attachment.

Adapters

In an embodiment of the method, an adapter may be attached to one or both ends of each of the multiple polynucleotides. The method may comprise an initial step of attaching an adapter to one or both ends of the multiple polynucleotides. The initial step may further comprise binding the enzyme to the adapter. Alternatively, the enzyme may be pre-bound to the adapter. Thus, the method may comprise an initial step of attaching an adapter having the enzyme pre-bound thereto to one or both ends of each of the multiple polynucleotides under conditions where the enzyme does not move along the polynucleotides. The enzyme may be stalled on the adapter. The adapter may be stalled by virtue of the absence of fuel and/or a necessary cofactor. The adapter may be stalled in the presence of fuel, using a stall that can be removed/overcome to initiate movement of the enzyme (e.g. by toehold displacement).

The same adapter may be added to both ends of the multiple polynucleotides. Alternatively, different adapters may be added to the two ends of each of the multiple polynucleotides. An adapter may be added to just one end of each of the multiple polynucleotides. Methods of adding adapters to polynucleotides are known in the art. Adapters may be attached to polynucleotides, for example, by ligation, by click chemistry, by tagmentation, by topoisomerisation or by any other suitable method.

The adapter is preferably capable of being attached to the end of a polynucleotide to which a nucleic acid handling enzyme can bind. The adapter is preferably synthetic or artificial. The adapter preferably comprises a polymer. The polymer is preferably a polynucleotide. The polynucleotide adapter may comprise DNA, RNA, modified DNA (such as a basic DNA), RNA, PNA, LNA, BNA and/or PEG. The adapter more preferably comprises single stranded and/or double stranded DNA or RNA. The polynucleotide may be of any suitable length, for example from about 4 to about 300, such as about 5 to about 200, about 10 to about 100, or about 20 to about 50 nucleotides in length.

The adapter may comprise a single stranded polynucleotide to which the nucleic acid handling enzyme is bound.

The adapter used for selection may be designed to facilitate the subsequent attachment of selected polynucleotides to further adapters, such as sequencing adapters. The adapter may, for example, comprise a single-stranded overhang or chemical group (e.g. click chemistry) for efficient attachment to a further adapter.

In one embodiment, the adapter is a Y adapter. A Y adapter and/or the bridging moiety adapter are typically polynucleotide adapters. A Y adapter is typically double stranded and comprises (a) at one end, a region where the two strands are hybridised together and (b), at the other end, a region where the two strands are not complementary. The non-complementary parts of the strands form overhangs. The presence of a non-complementary region in the Y adapter gives the adapter its Y shape since the two strands typically do not hybridise to each other unlike the double stranded portion. A nucleic acid handling enzyme may be bound to an overhang and/or to the double stranded region. In one embodiment, a first enzyme is bound to the double stranded region and a second enzyme is bound to an overhang. The second enzyme on the overhang is preferably stalled by a spacer. In one embodiment the Y adapter comprises a membrane anchor or a pore anchor. The anchor may be attached to a polynucleotide that is complementary to and hence that is hybridised to the overhang which an enzyme is not bound. One of the non-complementary strands Y adaptor typically comprises a leader sequence, which when contacted with a transmembrane pore is capable of threading into the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide.

The leader preferably comprises a polynucleotide and more preferably comprises a single stranded polynucleotide. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 120, 30 to 100, 40 to 80 or 50 to 70 nucleotides in length.

In one embodiment the adapter is a hairpin loop adapter. A hairpin loop adapter is an adapter comprising a single polynucleotide strand, wherein the ends of the polynucleotide strand are capable of hybridising to each other, or are hybridized to each other, and wherein the middle section of the polynucleotide forms a loop. Suitable hairpin loop adapters can be designed using methods known in the art. The loop may be any length. The loop is preferably from about 2 to 400, from 5 to 300, from 10 to 200, from 20 to 100 nucleotides or from 30 to 50 in length. The double stranded section of the adapter formed by two hybridized sections of the polynucleotide strand is called a stem. The stem of the hairpin loop is preferably from 4 to 200, such as 5 to 150, 10 to 100, 20 to 90, 30 to 80, 40 to 70 or 50 to 60 nucleotide pairs in length. Where a nucleic acid handling enzyme is bound to or binds to a hairpin adapter, it typically binds to the loop of the hairpin, rather than to the stem.

If the multiple polynucleotides are double stranded, a Y adapter may be added to one end and a hairpin loop adapter to the other end. In this embodiment, an enzyme may be bound to the Y adapter and/or to the hairpin adapter.

The adapter may comprise a second nucleic handling enzyme, preferably a helicase that is stalled on the adapter, for example by or at a spacer.

The adapters may be attached to the multiple polynucleotides in any manner. The adapters are preferably covalently attached to the target polynucleotide.

The adapters may be ligated to the target polynucleotide. The adapters may be ligated to either end of the polynucleotide, i.e. the 5' or the 3' end, or to both ends of the polynucleotide i.e. to the 5' end and to the 3' end. The adapters may be ligated to the polynucleotide using any method known in the art. The adapter may be ligated to the polynucleotides in the absence of ATP or using gamma-S-ATP (ATPγS) instead of ATP. It is preferred that the adapter is ligated to the polynucleotides in the absence of ATP where the nucleic acid handling enzyme is bound to the adapter.

The adapter may be ligated using a ligase, such as T4 DNA ligase, E. coli DNA ligase, Taq DNA ligase, Tma DNA ligase and 9° N DNA ligase. The ligase may be removed from the sample before step (i) of the method. The adapter may be attached using a topoisomerisase. The topoisomerase may, for example be a member of any of the Moiety Classification (EC) groups 5.99.1.2 and 5.99.1.3.

The inventors have devised an adapter which has bound thereto: a first nucleic acid handling enzyme; and a second nucleic acid handling enzyme, wherein the second nucleic acid enzyme is bound such that its movement along the adapter is hindered or prevented until it is brought into contact with a transmembrane pore under an applied potential, and wherein the second nucleic acid handling enzyme does not hinder movement of the first nucleic acid handling enzyme. In this embodiment, the adapter preferably comprises a polynucleotide and/or the second nucleic acid enzyme is preferably a translocase or helicase. The first and second nucleic acid handling enzymes may be the same or different. For example, the first enzyme may be a translocase, helicase or polymerase and the second enzyme may be a translocase or helicase. Where both the first and second enzymes are both translocases or helicases, they may be the same or different translocases or helicases.

Movement of the second enzyme may be hindered or prevented by being stalled at a spacer, for example as disclosed in WO 2014/135838. Any configuration of enzymes and spacers disclosed in WO 2014/135838 may be used in the method of separating polynucleotides.

The spacer is preferably part of the adapter, for instance the spacer may interrupt the polynucleotide sequence in the adapter. There may be any number of spacers in the adapter, such as 1, 2, 3, 4, 5, 6, 7, 8, 9, 10 or more spacers. There are preferably one, two, four or six spacers in the target polynucleotide. The one or more spacers are preferably located between the first and second enzymes on the adapter. The first enzyme is preferably on the side of the spacer that is towards the end of the adapter that is attached to, or is for attachment to, a polynucleotide. The spacer is preferably positioned between the second enzyme and the end of the adapter that is attached to, or is for attachment to, a polynucleotide. Alternatively, the second enzyme may be positioned on the spacer.

The spacer provides an energy barrier which the second enzyme cannot overcome even in the presence of fuel and the necessary coenzymes and/or cofactors. The spacer may stall the second enzyme by reducing the traction of the enzyme (for example the bases from the nucleotides in the spacer may be missing) or by physically blocking movement of the one or more helicases (for example, the spacer may comprise a bulky chemical group).

The spacer may comprise any molecule or combination of molecules that hinders or prevents the second enzyme from moving along the target polynucleotide. It is straightforward to determine whether or not an enzyme is stalled at a spacer, in the absence of a transmembrane pore and an applied potential. For example, the ability of an enzyme to move past a spacer and displace a complementary strand of DNA can be measured by polyacrylamide gel electrophoresis (PAGE).

The spacer typically comprises a linear molecule, such as a polymer. The spacer typically has a different structure from the target polynucleotide. For instance, if the target polynucleotide is DNA, the one or more spacers are typically not DNA. In particular, if the target polynucleotide is deoxyribonucleic acid (DNA) or ribonucleic acid (RNA), the spacer preferably comprise peptide nucleic acid (PNA), glycerol nucleic acid (GNA), threose nucleic acid (TNA), locked nucleic acid (LNA) or a synthetic polymer with nucleotide side chains. The spacer may comprise one or more nucleotides in the opposite direction from other nucleotides in the adapter. For example, the spacer may comprise one or more nucleotides in the 3' or 5' direction when the polynucleotide is in the 5' to 3' direction.

The spacer preferably comprises one or more nitroindoles, such as 5-nitroindoles, inosines, acridines, 2-aminopurines, 2-6-diaminopurines, 5-bromo-deoxyuridines, inverted thymidines (inverted dTs), inverted dideoxy-thymidines (ddTs), dideoxy-cytidines (ddCs), 5-methylcytidines, 5-hydroxymethylcytidines, 2'-O-Methyl RNA bases, Iso-deoxycytidines (Iso-dCs), Iso-deoxyguanosines (Iso-dGs), iSpC3 groups (i.e. nucleotides which lack sugar and a base), photo-cleavable (PC) groups, hexandiol groups, spacer 9 (iSp9) groups, spacer 18 (iSp18) groups, a polymer or thiol connections. The spacers may comprise any combination of these groups. Many of these groups are commercially available from IDT® (Integrated DNA Technologies®).

The spacer may contain, for example, 2, 3, 4, 5, 6, 7, 8, 9, 10, 11, 12 or more 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, 2, 3, 4, 5, 6, 7, 8, 9, 10, 11, 12 or more. The spacer preferably comprises 2, 3, 4, 5, 6, 7, 8 or more iSp9 groups and/or 2, 3, 4, 5 or 6 or more iSp18 groups. The most preferred spacer is four iSp18 groups.

Where the spacer comprises a polymer, the polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The spacer may comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into target polynucleotides by removing the nucleobases from one or more adjacent nucleotides. For instance, polynucleotides may be modified to include 3-methyladenine. 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The second enzyme may be stalled before or on a linear molecule spacer. If a linear molecule spacer is used, the adapter preferably comprises a double stranded region of polynucleotide adjacent to the end of the spacer closest to the end of the adapter which is attached to, or is for attachment to, the polynucleotide. A hybridized double stranded region preferably terminates at the spacer and the strand that does not comprise the spacer preferably forms an overhang adjacent to the spacer. A further polynucleotide strand may be hybridized to the overhang to form a further double stranded region. The further double stranded region typically helps to stall the second enzyme on the spacer. The further polynucleotide is typically formed from the same nucleotides as the target polynucleotide, but may be formed from different nucleotides. For instance, the further polynucleotide may be formed from locked nucleic acid (LNA) or bridged nucleic acid (BNA).

If a linear molecule spacer is used, the adapter preferably comprises a blocking molecule at the end of the spacer. The blocking molecule may help to ensure that the second enzyme remains stalled on the spacer. The blocking molecule may be any chemical group which physically causes the one or more helicases to stall. The blocking molecule may be a double stranded region of polynucleotide. Examples of suitable blocking polynucleotides are disclosed in the Examples.

Suitable chemical groups include pendant chemical groups. The chemical group may be attached to one or more nucleobases in the target polynucleotide and/or to the polynucleotide backbone. Any number of chemical groups may be present, such as 1, 2, 3. 4. 5, 6, 7, 8, 9, 10, 11, 12 or more. Examples of suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Where more than one spacer is present in an adapter they may be the same or different. For example, one spacer may comprise one of the linear molecules discussed above and another spacer may comprise one or more chemical groups which physically stall the second enzyme. A spacer may comprise any of the linear molecules discussed above and one or more chemical groups, such as one or more a basics and a fluorophore.

Most nucleic acid handling enzymes, such as helicases, bind and move along DNA and so may be stalled using anything that is not DNA.

In the absence of a transmembrane pore and an applied potential, the spacer is preferably capable of stalling the second enzyme in the presence of free nucleotides and/or the presence of a cofactor.

Step (i) of the method of separating polynucleotides is carried out in the presence of fuel (free nucleotides) and a cofactor. The length and characteristics of the spacer are typically chosen to ensure that the one or more helicases are stalled on the adapter during the method.

The ability of a spacer to stall an enzyme may be affected by salt concentration. The higher the salt concentration used in the method of the invention, the shorter the one or more spacers need to be. In the absence of a transmembrane pore and an applied potential, the spacer is preferably capable of stalling the second-enzyme at a salt concentration of less than about 100 mM.

Examples of spacers that can be used to stall an enzyme that process DNA in the presence of free nucleotides and a cofactor include: at 1M salt, 4 iSpC3 groups or 2 iSp18 groups; at 100-1000 mM salt, 4 iSp18 groups or 6 iSp9 groups; at <100-1000 mM salt, 6 iSp18 groups, 12 iSpC3 groups or 20 iSpC3 groups.

An enzyme can be 'pushed over' a stalling chemistry by annealing a DNA strand behind the enzyme, e.g. by toehold displacement. Alternatively, an enzyme can be 'stalled' using a condition in which it is unable to translocate. For example, the adapter may be kept in a pH at which the enzyme is unable to translocate and/or bind fuel. A small molecule inhibitor could alternatively be used to stall an enzyme.

In one embodiment, the adapter further comprises a membrane anchor or pore anchor. The anchor is preferably present when a first enzyme and a second stalled enzyme are bound to the adapter. Suitable anchors are known in the art, as described, for example, in WO 2012/164270 and WO 2015/150786.

An adapter useful in the selection method may comprise a tag. The tag may be hybridized to the adapter or may be attached to the enzyme.

Suitable tags are known in the art. Examples of suitable tags include, but are not limited to, biotin, a selectable polynucleotide sequence, antibodies, antibody fragments, such as Fab and ScSv, antigens, polynucleotide binding proteins, poly histidine tails and GST tags. Biotin specifically binds to a surface coated with avidins, such as streptavidin. Selectable polynucleotide sequences specifically bind (i.e. hybridise) to a surface coated with complementary sequences.

The adapter and/or the tag may comprise a region that can be cut, nicked, cleaved or hydrolysed. Such a site can be designed to allow the polynucleotides that meet the selection criteria, or polynucleotide that do not meet the selection criteria, to be removed from the surface, beads or column to which they are bound. Suitable sites are known in the art. Suitable sites include, but are not limited to, an RNA region, a region comprising desthiobiotin and streptavidin, a disulphide bond, a photocleavable region and a restriction enzyme site, or other site that is selectively cleaved by an enzyme.

The adapter may, in addition to or instead of a tag, comprise a hidden site for attaching a further polynucleotide and/or other molecule, such as, for example, a protein. The adapter may, in addition to or instead of a tag, comprise an exposed site for attaching a further polynucleotide and/or other molecule, such as, for example, a protein. The further polynucleotide or other molecule, such as, for example, a protein is used to create a selection bias.

A site for attaching a further polynucleotide may, for example, be a single stranded region that is capable of hybridising to a complementary polynucleotide strand or to a strand comprising or consisting of universal bases, such as inosines. The complementary polynucleotide strand may be DNA, RNA, a DNA/RNA hybrid, PNA, LNA, BNA and/or. a strand comprising or consisting of modified bases. The modified bases may, for example, be abasic nucleotides, such as nucleotides in which the nucleobase is replaced by —H (idSp) or —OH. The modified bases may, for example, include one or more of 3-methyladenine, 7-methylguanine, 1,N6-ethenoadenine inosine or hypoxanthine and the nucleobases may be removed from these nucleotides using Human Alkyladenine DNA Glycosylase (hAAG). The polynucleotides may be modified to include uracil and the nucleobases removed with Uracil-DNA Glycosylase (UDG). The modified bases may, for example, be 2'-O-Methyl (2'OMe) and/or 2'-fluoro bases. The complementary or universal strand may be present in an adapter, such as a Y adapter for characterising the selected polynucleotides using a transmembrane pore, e.g. the further polynucleotide may be an adapter, such as a Y adapter.

A site for attaching a molecule, may for example, be a single stranded DNA section that can bind, when exposed, to a single stranded DNA binding protein (SSB), such as the *E. coli* single stranded binding protein.

The further polynucleotide or other molecule, such as, for example, a protein that is used to create a selection bias may, for example, be tagged, allow ligation to the polynucleotides to which the strand is hybridised, or conversely to prevent ligation to the polynucleotides to which the strand is hybridised, allow digestion, or conversely prevent digestion. The ligation may be direct ligation, for example using a ligase or indirect ligation such as using click chemistry.

The adapter may, in addition to or instead of a tag, comprise a hidden site that can be ligated to another strand when the site becomes exposed. The adapter may, in addition to or instead of a tag, comprise an exposed site for attaching a further polynucleotide that can be ligated to another strand.

The adapter may, in addition to or instead of a tag, comprise a hidden site that allows digestion of the strand when it becomes exposed. The adapter may, in addition to or instead of a tag, comprise an exposed site that allows digestion of the strand when it becomes exposed.

The adapter may, in addition to or instead of a tag, contain a chemical group suitable for click chemistry attachment that is hidden or exposed.

The hidden site may comprise a secondary structure such as a hairpin. For example, a hairpin could be ligated shut by the action of the enzyme, for example to prevent attachment of a sequencing adapter or to allow rolling circle amplification of a specific template.

An exposed site may be removed from polynucleotides which do not meet the section criteria during the separation method. A hidden site is typically revealed in polynucleotides which do meet the selection criteria.

The adapter may be single stranded and/or double stranded. The adapter may, for example, contain both single stranded and double stranded sections. The adapter may attach to one strand, or preferably to both strands of a double stranded polynucleotide. An adapter may be attached to one or both ends of each of the multiple polynucleotides.

Defined Time Period

In step (i) of the selection method, the enzyme is allowed to move along the multiple polynucleotides for a defined time period. The length of the defined time period is based on the selection criteria, for example the length of the polynucleotides it is wished to select/deselect, on the enzyme chosen as the nucleic acid handling enzyme and on the reaction conditions. It is within the routine skill of a person skilled in the art to determine a suitable defined time period. For example, the skilled person would be able to take a sample comprising a polynucleotide of the desired length and to allow an enzyme to move along the control polynucleotide for various time periods under the conditions to be used in the method. The skilled person would then be able to determine after what time period the enzyme moves off the end of the polynucleotide. The defined time period can then be chosen to be less than the time taken for the enzyme to move off the end of the control polynucleotide of the desired length. The selection method may then be used to separate polynucleotides of the desired length from shorter polynucleotides.

The defined time period may be of any length, for example from about 1 second to about 14 days or longer, about 5 seconds to about 10 days, about 10 seconds to about 7 days, about 20 seconds to about 5 days, about 25 seconds to about 2 days or about 1 minute to about 1 day.

Starting Time Period

Movement of the enzyme along the multiple polynucle-otides may be initiated in any suitable way. The method of initiating movement will depend on how the method is being carried out. In an embodiment where one or more molecules of the enzyme are attached to the multiple polynucleotides prior to step (i), the defined time period is typically started by initiating movement of the enzyme. Movement of the enzyme may be initiated, for example, by changing the conditions so that the enzyme is able to move. For example, a nucleotide that provides energy for the enzyme, a co-enzyme and/or a co-factor may be added to initiate move-ment of the enzyme. Alternative examples of ways in which movement of the enzyme may be initiated include changing the pH, temperature and/or salt concentration, and/or push-ing the enzyme over a spacer that has been used to stall the enzyme by hybridisation of a strand behind the enzyme, e.g. by toehold displacement.

In an embodiment where the enzyme is not pre-bound to the multiple polynucleotides prior to step (i), the defined time period is typically started by contacting the multiple polynucleotides with the enzyme. In this embodiment, the multiple polynucleotides are contacted with the enzyme under conditions suitable for the enzyme to move along the nucleotides. For example, the enzyme is added under pH, temperature and salt conditions amenable to movement of the enzyme. A nucleotide that provides energy for the enzyme and any necessary co-enzymes and/or co-factors are also typically added with the enzyme, or are already present in the sample.

In an embodiment of the invention where prior to step (i) the enzyme is allowed to bind to the multiple polynucle-otides from solution, at the start of the defined time period additional molecules of the enzyme are prevented from binding to the multiple polynucleotide. This may be achieved in any suitable way. For example, the enzymes that are not bound to the multiple polynucleotides may be sequestered by binding to a capture strand that is added to the mixture at the start of the defined time period. In one embodiment, capture strand or another molecule that sequesters unbound enzyme may be added together with, for example, a nucleotide that provides energy for the enzyme, a co-enzyme and/or a co-factor. Alternatively or addition-ally, the salt concentration can be adjusted, typically by adding salt, such that rebinding of enzymes to the poly-nucleotides is prevented. Alternatively or additionally, the enzyme can be closed around the polynucleotide before initiation of the defined time period. This can be achieved, for example by ligating an adapter that contains the enzyme binding site to the ends of the strands, then adding the enzyme in solution, closing all of the enzymes, for example with tetramethylazodicarboxamide (TMAD) and increasing the salt concentration to prevent binding of other enzymes in solution.

An alternative to adding a capture strand may, where the multiple polynucleotides are bound to a bead, column or surface via an adapter, to wash away any unbound enzyme and add in solution any necessary fuel, coenzymes and/or cofactors.

Free Nucleotides and Co-Factors

Movement of the enzyme can be controlled by adding or removing fuel and/or co-enzymes/co-factors. Fuel is typi-cally free nucleotides or free nucleotide analogues. The enzyme may be added to/bound to the multiple polynucle-otides in the absence of free nucleotides or free nucleotide analogues and in the absence of any co-enzymes and/or co-factor required for enzyme movement. The free nucleo-tides may be one or more of, but are not limited to, adenosine monophosphate (AMP), adenosine diphosphate (ADP), adenosine triphosphate (ATP), guanosine monophosphate (GMP), guanosine diphosphate (GDP), guanosine triphos-phate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cyti-dine diphosphate (CDP), cytidine triphosphate (CTP), cyclic adenosine monophosphate (cAMP), cyclic guanosine mono-phosphate (cGMP), deoxyadenosine monophosphate (dAMP), deoxyadenosine diphosphate (dADP), deoxyade-nosine triphosphate (dATP), deoxyguanosine monophos-phate (dGMP), deoxyguanosine diphosphate (dGDP), deox-yguanosine triphosphate (dGTP), deoxythymidine monophosphate (dTMP), deoxythymidine diphosphate (dTDP), deoxythymidine triphosphate (dTTP), deoxyuri-dine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the polynucle-otide binding protein to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Stopping Time Period

The defined time period is stopped by inhibiting move-ment of the enzyme.

Movement of the enzyme may be stopped by any suitable method such as: (a) removing a nucleotide that provides energy for the enzyme, a coenzyme and/or a cofactor; (b) adding an enzyme inhibitor; (c) changing the pH, tempera-ture or salt concentration; and/or (d) denaturing the enzyme.

In an embodiment where the multiple polynucleotides are bound to a bead, column or surface, for example via a tag on the enzyme or a tag in an adapter, the defined time period may be stopped by washing the bead, column or surface. This may serve to remove polynucleotides that do not meet the selection criteria. The reaction may then be restarted by adding a fuel, co-enzyme and/or co-factor in order to further separate the multiple polynucleotides remaining on the bead, column or surface. Situations where this may be desirable are shown in the Figures.

In one embodiment, the defined time period is stopped when the amount of fuel, e.g. amount of a nucleotide that provides energy for the enzyme, is depleted causing move-ment of the enzyme to stop. The fuel may be depleted by movement of the enzyme along the multiple polynucle-otides. Alternatively, fuel may be depleted in another way, such as by adding a competitor enzyme, for example an enzyme with higher affinity for the fuel, to deplete the fuel and cause enzyme movement to stop.

In an embodiment where the adapter comprises a hidden tag that is revealed when a molecule of the enzyme reaches the end of a polynucleotide, the defined time period may be stopped by contacting the reaction mixture with beads, a column or surface such that shorter polynucleotides with the tag revealed may be removed, leaving the longer polynucle-otides that meet the selection criteria in solution.

In an embodiment where the adapter or enzyme is tagged, the multiple polynucleotides may be bound to beads, a column or a surface at the start of step (i). The reaction may then be stopped by washing the beads, column or surface. This will remove any fuel, coenzymes and/or cofactors required for enzyme movement. At the same time polynucleotides are not bound to the bead, surface or column may be separated from those that are bound.

In one embodiment, the defined time period is determined by the amount of fuel and/or co-factor present in the reaction conditions during the selection. The time period ends when the enzyme runs out of fuel and/or cofactor and can no longer move along the polynucleotides. It is within the routine skill of a person skilled in the art to determine the rate of fuel turnover by the enzyme. By controlling the amount of fuel, polynucleotides and/or enzyme present in the reaction the skilled person would be able to control the length of time for which the enzyme will be active and hence define a time period during which enzyme movement occurs. Typically, in this embodiment, the amount of fuel is limited so that the fuel is depleted within a defined time period.

Selecting

The method may be used to select multiple polynucleotides that meet the selection criteria. A subgroup of the multiple polynucleotides in a sample may be selected. In the method more than one polynucleotide may be selected, such as at least 2, at least 3, at least 4, at least 5, for example from about 10 to about 100,000, about 20 to about 10,000, about 30 to about 1,000 or about 50 to about 500 polynucleotides.

The selection method is used to distinguish polynucleotides having different physical characteristics. In one embodiment, the method comprises a step of separating selected polynucleotides from unselected polynucleotides. A number of different selections could be performed in combination. In one embodiment, the method selects polynucleotides that can then be separated and/or selectively modified based on their lengths. Preferably, the method is used to select long polynucleotides. The length of the selected polynucleotides may vary depending on what is desired. The method may be adjusted such that polynucleotides of the desirable length are selected. For example, the method may be used to select polynucleotides having a length of at least 1 kb, 10 kb, 50 kb, 100 kb, 1,000 kb, 10,000 kb, 100,000 kb, 200,000 kb or 250,000 kb.

In one embodiment, the method may be used to distinguish damaged polynucleotides from undamaged polynucleotides. The undamaged or damaged polynucleotides can be selected and separated. The damaged or undamaged polynucleotides can be selectively modified. A damaged polynucleotide is any polynucleotide which comprises an alteration in its chemical structure, for example, an alteration in the chemical structure of DNA or RNA. Polynucleotide damage includes a break in one strand of a double stranded polynucleotide, one or more base missing from the polynucleotide, or one or more chemically altered base. Thus, the method can be used to separate polynucleotides with nicked strands from intact polynucleotides. A polynucleotide with a nicked strand may, in one embodiment, be a double stranded DNA in which there is at least one break in one of the DNA strands. The method can be used to select intact polynucleotides. Examples of how the method may be implemented to separate damaged polynucleotides from undamaged polynucleotides are shown in the Figures. The Figures also show how polynucleotides of different lengths may be separated.

The method may be used to select polynucleotides that fall within a particular "window". For example, the method may be carried out two or more times to select a polynucleotide within a defined range of lengths, i.e. by removing polynucleotides that are shorter than the desired length and then polynucleotides that are longer than the desired length or vice versa. Additionally, or alternatively, the method steps may be carried out two or more times to separate damaged polynucleotides from undamaged polynucleotides and to select polynucleotides of a desired length. Steps (i) and (ii) of the method may be repeated once, twice, three time or more, such as four, five or six times. By repeating the method, polynucleotide fractions may be obtained, wherein each fraction contains polynucleotides of a different length from the other fractions.

The method selects the polynucleotides based on whether the enzyme reaches the end of the polynucleotides and/or whether the enzyme unbinds from the polynucleotides. This selection may be achieved in any suitable way. Thus, the selection of polynucleotides may be based on certain polynucleotides in the sample having an enzyme bound thereto at the end of the defined time period whilst other polynucleotides in the sample do not. Other examples of how the selection may be achieved include end modification and enzyme tagging. In one embodiment, the method is used to separate polynucleotides comprising adapters at both ends from un-adapted polynucleotides and/or polynucleotides comprising an adapter at only one end.

End modification allows polynucleotides which have had an enzyme move off the end to be separated from polynucleotides which have not had an enzyme move off the end or to be selected for further processing and/or characterisation without being physically separated from other polynucleotides in the sample. In one embodiment of end modification, an adapter comprising an end signal is attached to one or both ends of each of the multiple polynucleotides. The end signal may, for example, be a selection tag, a hidden site for attaching a further polynucleotide, an exposed site for attaching a further polynucleotide or a cap preventing digestion by an exonuclease. Where such an end signal is used, in step (i) the selection tag is displaced, the hidden site is revealed, the exposed site is removed or the cap is removed when a molecule of the enzyme reaches the end of the polynucleotide. In step (ii), the selection tag, hidden site, exposed site or uncapped end may then be used to separate the polynucleotides.

Where the end signal is a selection tag, the multiple polynucleotides may be bound to a bead, column or surface via the selection tag. Displacement of the selection tag by the enzyme then results in the polynucleotide to which the enzyme is no longer attached being released from the bead, column or surface. In this embodiment, the polynucleotides that remain bound to the bead, column or surface after washing may be further separated by repeating steps (i) and (ii). When steps (i) and (ii) are repeated, the polynucleotides meeting the selection criteria may be those eluted from the bead, column or surface, or may be those remaining bound to the bead, column or surface. When only polynucleotides meeting the selection criteria remain bound to the bead, column or surface, those polynucleotides may be recovered from the bead, column or surface, for example, by: restarting movement of the enzyme and allowing the enzyme to reach the ends of the polynucleotides; or unbinding the polynucleotides from the bead, column or surface. Unbinding may be achieved by standard methods known in the art. For example, the adapter may comprise a cleavage site that can be used to release the polynucleotides.

In another embodiment that uses an end signal that is a selection tag, the selection tag may be hidden in the adapter.

For example, the selection tag could be hidden by being bound to a binding partner. For example, if the tag is biotin, it could be bound to DNA or an avidin, such as streptavidin. When the enzyme reaches the end of a polynucleotide, the partner of the binding tag may be removed. A bead, surface or column having the binding tag partner attached thereto could then be used to select, or remove, polynucleotides in which the end tag has been revealed.

A hidden site that functions as an end signal may be any site, such as a DNA sequence, that enables the DNA to be ligated or attached in any way to a further polynucleotide or to another molecule. For example, the hidden site may be a site enabling attachment to another molecule via click chemistry. Methods of using click chemistry attachment are described in, for example, International patent application no. PCT/GB2017/051493.

Click chemistry is advantageous because it does not typically involve the use of enzymes (Kolb et al (2001) Angew. Chem. Int. Ed. 40 2004-2021). Suitable example of click chemistry include, but are not limited to a copper-free variant of the 1,3 dipolar cycloaddition reaction, where an azide reacts with an alkyne under strain, for example in a cyclooctane ring; the reaction of an oxygen nucleophile on one linker with an epoxide or aziridine reactive moiety on the other; and the Staudinger ligation, where the alkyne moiety can be replaced by an aryl phosphine, resulting in a specific reaction with the azide to give an amide bond.

Preferably the click chemistry reaction is the Cu (I) catalysed 1,3 dipolar cycloaddition reaction between an alkyne and an azide. In a preferred embodiment, the first group is an azide group and the second group is an alkyne group. Nucleic acid bases incorporating azide and alkyne groups in preferred positions are known (for example in Kocalka et al (2008) Chembiochem. 9(8):1280-5). Alkyne groups are available commercially from Berry Associates (Michigan, USA) and azide groups are synthesised by ATDBio.

Copper free click chemistry can be used. It is fast, clean and not poisonous towards proteins. A good example of this is maleimide or iodoacetamide linking with a cyclooctyne functional group (DIBO). Other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

Preferably the reactive groups are azide and hexynl groups such as 3AzideN and 5'-hexynl-G. Preferred pairs of non-covalent reactive groups include, but are not limited to, (i) Ni-NTA and polyhistidine, such as 6×His, and (ii) cyclodextrin and adamantine.

The hidden site may be hidden, or protected, in any way. For example, a molecule may be used to hide, or occlude, a click reactive group. Movement of the enzyme may remove the molecule and reveal the reactive group. Any suitable molecule may be used. For example, pyrene may be used to stack with the DBCO. If the hidden site comprises a Ni-NTA group (which can attach to polyhistidine, such as 6×His), the hidden site may be protected with polyhistidine, such as 6×His, in the same target polynucleotide and vice versa, i.e. the hidden site may comprise polyhistidine, such as 6×His, and may be protected by Ni-NTA groups. If the hidden site comprises cyclodextrin (which can attach to amantadine in the subsequent polynucleotide), the hidden site may be protected by amantadine in the same target polynucleotide or vice versa. The hidden site and the protecting molecule may be present on opposite strands of an adapter and hence on opposite stands of a polynucleotide to which the adapter is attached. Separation of the strands by the enzyme may then separate the protecting molecule from the hidden site and reveal the hidden site.

The hidden site may be protected by hybridisation to a protecting polynucleotide. The protecting polynucleotide may be removed when the enzyme reaches the end of the polynucleotide. In one example, the protecting polynucleotide may prevent the action of a single strand ligase on the hidden site. Release of the protecting polynucleotide would reveal the hidden site as a substrate for the ligase.

The end signal may be created by movement of the enzyme over the adapter at the end of the polynucleotide altering the secondary or tertiary structure of the polynucleotide. For example, movement of the enzyme may unwind a hairpin or quadruplex to alter the ability of the adapter to move a further polynucleotide.

In one embodiment, in step (ii) of the method polynucleotides to which the enzyme remains bound are separated from polynucleotides to which the enzyme is not bound. One way of achieving this is to use a tagged enzyme.

In one embodiment, a tagged enzyme is attached to an adapter, such that at the start of step (i) of the method, one molecule of enzyme moves along the polynucleotide, or one molecule of the enzyme moves along each strand of the polynucleotide in opposite directions. If the tagged enzyme remains on the polynucleotide at the end of the defined time period, the polynucleotide is tagged via the tag on the enzyme and can be separated from shorter polynucleotides on which no enzyme found.

In another embodiment, where multiple molecules of the tagged enzyme are bound to the multiple polynucleotides, all of the molecules of the tagged enzyme present on the polynucleotide move along the polynucleotides. If any molecules of tagged enzyme remain on the polynucleotide at the end of the defined time period, the polynucleotide is tagged via the tag on the enzyme and can be separated from shorter polynucleotides from which all molecules of the tagged enzyme have moved off.

In one embodiment, the tag on the enzyme may be used to bind the enzyme to a bead, column or surface. The enzyme may be bound to the bead, column or surface prior to carrying out step (i) of the method. Alternatively, the bead, column or surface may be used in step (ii) of the method to bind polynucleotides which retain a tagged enzyme. In an embodiment where the enzyme is bound to beads, a column or a surface prior to step (i), the defined time period of step (i) can be terminated by quenching the solution or by removing the beads, column or surface from the reaction solution containing the necessary fuel, co-enzymes and/or co-factors necessary for enzyme movement. Steps (i) and (ii) can be repeated to collect multiple fractions of different lengths and/or to select polynucleotides of a certain length and/or to separate out damaged and undamaged polynucleotides.

In one embodiment, the adapter may comprise a sequence that is capable of hybridising to a complementary polynucleotide strand, which complementary strand is tagged, for example, with biotin or desthiobiotin. The complementary strand may comprise part of the adapter, and/or may be pre-bound to a bead, column or surface. The adapter may be used to bind the multiple polynucleotides to a bead, column or surface. Movement of the enzyme in step (i) then displaces polynucleotides that are too short to meet the selection criteria from the bead, column or surface. The polynucleotides remaining bound to the beads, column or surface may be damaged or undamaged polynucleotides. Steps (i)

and (ii) may be repeated to select only for undamaged strands. The damaged strands will remain bound to the bead, column or surface whilst the undamaged strands will be released.

In one particular embodiment, the adapter may be ligated to, or comprise a DNA containing a binding site and a priming site for a strand displacing DNA polymerase. Movement of the polymerase along polynucleotides which are sufficiently short for the polymerase to reach the end in the defined time period may be used to displace a biotinylated strand polynucleotide. Alternatively, the polymerase may be tagged.

In methods which use a selection tag, an extraction medium is typically used to separate tagged polynucleotides from untagged polynucleotides. Any suitable extraction medium may be used. Examples of suitable extraction media include beads, columns and surfaces. In one embodiment, the surface may be a membrane comprising a transmembrane pore.

The enzyme or adapter can be pre-bound to an extraction medium. Use of an extraction medium enables washing to: quench by flushing; remove unwanted polynucleotides that do not meet the selection criteria; and/or elute desired polynucleotides that do meet the selection criteria.

Hence, the defined time period may be stopped by flushing a bead, column or surface and/or polynucleotides not bound to the bead, column or surface may be removed or eluted by washing the bead, column or surface at the end of the defined time period.

In one embodiment, the polynucleotides that remain bound to the bead, column or surface after washing are further separated by repeating steps (i) and (ii).

Polynucleotides that remain bound to the bead, column or surface may be recovered from the bead, column or surface by any suitable method, such as: restarting movement of the enzyme and allowing the enzyme to reach the ends of the polynucleotides; unbinding the enzyme from the bead, column or surface; or unbinding the enzyme from the polynucleotides.

One example of an exposed site in an adapter is an overhang that allows efficient ligation to a further polynucleotide such as a sequencing adapter. If the enzyme reaches the end of the strand in the defined time period (i.e. when the strand is short), the adapter may fold into a conformation in which the overhang for ligation is no longer available. This will allow selection of strands of a desired length, but not to select for un-nicked strands. Alternatively, the enzyme may displace the strand containing the specific overhang. This alternative is particularly useful for adding sequencing adapters with a 5' overhang to the selected polynucleotides.

The end signal may, in one embodiment, be a cap preventing digestion by an exonuclease. Digestion by an exonuclease may be prevented by, for example, including one or more of the following in the adapter: phosphorothioate (PS) bonds at the 5' end and/or 3' end, typically at least 3 PS bonds at the 5' end and/or 3' end; 2'-O-Methyl (2'OMe) modified nucleotides at the 5' end and/or 3' end; 2-fluoro bases at the 5' end and/or 3' end: inverted dT and ddT at the 5' end and/or 3' end; phosphorylated 5' and/or 3' nucleotides; a spacer, such as a phosphoramidite C3 Spacer, at the 5' end and/or 3' end.

Selected DNA may be used for any purpose. Many platforms require intact/long DNA polynucleotides or indeed only short polynucleotide fragments. For example, the polynucleotides may be characterised, such as sequenced using any suitable sequencing method. Typically, any high throughput sequencing method may be used.

In one particular embodiment, the method may be used to select target polynucleotides for delivery to a transmembrane pore.

To achieve this, an adapter may be attached to each of the multiple polynucleotides, wherein a second nucleic acid handling enzyme is attached to the adapter and is stalled on the adapter such that it does not move along the polynucleotide in step (i).

Alternatively, step (ii) may comprise: binding the hidden or exposed site to an adapter comprising a single stranded leader sequence and optionally a membrane anchor or a transmembrane pore anchor, wherein a second nucleic acid handling enzyme is attached to the adapter and is stalled on the adapter; and bringing the sample into contact with a transmembrane pore.

Where the selected polynucleotides are bound to a bead, the polynucleotide may be contacted with the pore whilst still bound to the beads. The heads may be used to facilitate delivery of the selected polynucleotides to the pore, for example as disclosed in WO 2016/059375.

Where the polynucleotides are bound to a surface, the surface may be a membrane comprising the pore. The selection tag may, in this embodiment, be a membrane anchor, such as cholesterol. The membrane anchor may, for example, be bound to the enzyme, may be hidden in the adapter and revealed by enzyme reaching end, or may be present in the adapter and a cleavage site by which the adapter may be removed may be revealed by the enzyme reaching the end.

The membrane anchor may be a polypeptide anchor and/or a hydrophobic anchor that can be inserted into the membrane. The hydrophobic anchor is preferably a lipid, fatty acid, sterol, carbon nanotube, polypeptide, protein or amino acid, for example cholesterol, palmitate or tocopherol. The anchor may comprise thiol, biotin or a surfactant.

In one aspect the anchor may be biotin (for binding to streptavidin), amylose (for binding to maltose binding protein or a fusion protein), Ni-NTA (for binding to poly-histidine or poly-histidine tagged proteins) or peptides (such as an antigen).

The anchor may comprise a linker, or 2, 3, 4 or more linkers. Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The adapter may hybridise to a complementary sequence on a circular polynucleotide linker. The one or more anchors or one or more linkers may comprise a component that can be cut or broken down, such as a restriction site or a photolabile group. The linker may be functionalised with maleimide groups to attach to cysteine residues in proteins. Suitable linkers are described in WO 2010/086602.

The anchor is preferably cholesterol or a fatty acyl chain. For example, any fatty acyl chain having a length of from 6 to 30 carbon atom, such as hexadecanoic acid, may be used.

Examples of suitable anchors and methods of attaching anchors to adapters are disclosed in WO 2012/164270.

A method of characterising a polynucleotide is provided. The characterisation method comprises:

(i) carrying out a selection method as described herein;
  (ii) contacting a transmembrane pore with the selected polynucleotides;
  (iii) applying a potential difference across the transmembrane pore; and
  (iv) taking one or more measurements which are indicative of one or more characteristics of a polynucleotide moving with respect to the transmembrane pore and thereby characterising the polynucleotide.

The one or more characteristics may be selected from (i) the length of the polynucleotide, (ii) the identity of the polynucleotide, (iii) the sequence of the polynucleotide, (iv) the secondary structure of the polynucleotide and (v) whether or not the polynucleotide is modified.

The method characterisation typically comprises measuring the current passing through the transmembrane pore as the polynucleotide moves with respect to the transmembrane pore.

Transmembrane pores and nucleic acid handling enzymes are known in the art. Suitable membranes and devices are also known, as are methods for analysing the current signal to determine sequence and other characteristics of the polynucleotides.

Kits

A kit for separating polynucleotides is provided comprising one or more adapters for use in the separation method as defined herein; and any one or more, including any combination, of the following components:

an extraction medium;

a nucleic acid handling enzyme;

a nucleotide that provides energy for the enzyme, an enzyme cofactor and/or a coenzyme;

a solution comprising fuel and/or cofactor for the nucleic acid handling enzyme;

wash solution, which does not contain fuel and/or cofactor for the nucleic acid handling enzyme;

a site specific endonuclease; and/or a sequencing adapter.

The adapter may, for example, be an adapter comprising an end signal. The end signal may, for example, be a selection tag, a hidden site for attaching a further polynucleotide, an exposed site for attaching a further polynucleotide or a cap preventing digestion by an exonuclease.

The selection tag may be hidden in the adapter. For example, the selection tag could be hidden by being bound to a binding partner. For example, if the tag is biotin, it could be bound to DNA or an avidin, such as streptavidin. The selection tag may be a membrane anchor, such as cholesterol. The selection tag may, for example, be biotin (for binding to streptavidin), amylose (for binding to maltose binding protein or a fusion protein), Ni-NTA (for binding to poly-histidine or poly-histidine tagged proteins) or peptides (such as an antigen). The kit may further comprise a molecule that binds to the selection tag. The molecule that binds to the selection tag may be coupled to the extraction medium.

The hidden site may be any site, such as a DNA sequence, that enables the DNA to be ligated or attached in any way to a further polynucleotide or to another molecule. The adapter may, for example, have a single stranded overhang that can hybridise to the complementary sequence in a further polynucleotide. The overhang may have a length of from about 4 to about 15 nucleotides, such as about 6, 8, 10 or 12 nucleotides. The hidden site may be a site enabling attachment to another molecule via click chemistry. Suitable sites are disclosed above.

The hidden site may be hidden, or protected, for example, by a molecule that occludes the click reactive group. For example, pyrene may be used to stack with the DBCO. If the hidden site comprises a Ni-NTA group (which can attach to polyhistidine, such as 6×His), the hidden site may be protected with polyhistidine, such as 6×His, in the same target polynucleotide and vice versa, i.e. the hidden site may comprise polyhistidine, such as 6×His, and may be protected by Ni-NTA groups. If the hidden site comprises cyclodextrin (which can attach to amantadine in the subsequent polynucleotide), the hidden site may be protected by amantadine in the same target polynucleotide or vice versa. The adapter may comprise a hidden site on one strand and a protecting molecule on the opposite strand.

The hidden site may be protected by hybridisation to a protecting polynucleotide. The protecting polynucleotide may be removed when the enzyme reaches the end of the polynucleotide. The protecting polynucleotide may for example be at least partially complementary to a single stranded overhang sequence in the adapter, for example the protecting polynucleotide may have from about 70% to 100% identity to the overhang sequence, such as about 75%, 80%, 80% or 95% identity. In one example, the protecting polynucleotide may prevent the action of a single strand ligase on the hidden site. Release of the protecting polynucleotide would reveal the hidden site as a substrate for the ligase.

The end signal may be a secondary or tertiary structure such as hairpin or quadruplex that can be removed, such as unwound, by movement of the enzyme. One example of an exposed site in an adapter is an overhang that allows efficient ligation to a further polynucleotide such as a sequencing adapter. If the enzyme reaches the end of the strand in the defined time period (i.e. when the strand is short), the adapter may fold into a conformation in which the overhang for ligation is no longer available. This will allow selection of strands of a desired length, but not to select for un-nicked strands. Alternatively, the enzyme may displace the strand containing the specific overhang. This alternative is particularly useful for adding sequencing adapters with a 5' overhang to the selected polynucleotides.

The end signal may, in one embodiment, be a cap preventing digestion by an exonuclease. Digestion by an exonuclease may be prevented by, for example, including one or more of the following in the adapter: phosphorothioate (PS) bonds at the 5' end and/or 3' end, typically at least 3 PS bonds at the 5' end and/or 3' end; 2-O-Methyl (2'OMe) modified nucleotides at the 5' end and/or 3' end; 2'-fluoro bases; inverted dT and ddT at the 5' end and/or 3' end; phosphorylated 5' and/or 3' nucleotides; a spacer, such as a phosphoramidite C3 Spacer, at the 5' end and/or 3' end.

The nucleic acid handling enzyme may be any of the enzymes discussed above.

The extraction medium may be beads, a column or surface. The nucleic acid enzyme or adapter may be tagged. The tag (selection tag) is capable of binding to extraction medium. Extraction medium may be modified to facilitate binding of the tag. For example, coated with biotin where the tag is a strep tag.

In one embodiment, the adapter may comprise a sequence that is capable of hybridising to a complementary polynucleotide strand, which complementary strand is tagged, for example, with biotin or desthiobiotin. The complementary strand may comprise part of the adapter, and/or may be pre-bound to a bead, column or surface.

In one particular embodiment, the adapter may be ligated to, or comprise a DNA containing a binding site and a priming site for a strand displacing DNA polymerase.

The enzyme or adapter in the kit can be pre-bound to an extraction medium.

The hidden or exposed site may after separation of the polynucleotides be bound to one or more sequencing adapter, or otherwise modified for use in a method of characterisation or any other method requiring the polynucleotide(s). The kit may include one or more sequencing adapters. Suitable sequencing adapters are known in the art and others are described herein. The adapter comprising an end signal may be a sequencing adapter.

The following Examples illustrate the invention.

Example 1

This Example demonstrates that a polynucleotide may be selected based on its length using a DNA translocase. The method used corresponds to the embodiment outlined in FIG. 1.

Materials and Methods

Preparation of the Size Selection Adapter

The size selection adapter comprises a top strand (SEQ ID NO: 1), a bottom strand (SEQ ID NO: 2) and a blocker strand (SEQ ID NO: 3) annealed together at 4.72 µM, 5.66 µM and 5.66 µM respectively in 50 mM HEPES pH 8, 100 mM potassium acetate from 95° C. to 22° C. at 2° C. per minute. 40 µL of annealed DNA was added to 360 µL of a 4 µM DNA helicase (Dda) containing a strep-SUMO tag (SEQ ID NO: 4 below). The helicase was bound to the size selection adapter for 45 minutes at room temperature, and 5 µL of 8.1 mM Diamide (SIGMA-ALDRICH) was added. The sample was incubated at 35° C. for 60 minutes. 40 µL of 5 M NaCl and 15 µL of Nuclease free water (Ambion™) was added to the sample. The sample was incubated for 30 minutes at room temperature. The sample was purified on an HQ10 column, and the free annealed DNA and helicase bound annealed DNA were separated into different fractions. The helicase bound DNA is referred to below as the 'size selection adapter'.

Ligation of Size Selection Adapter to DNA 3608 ng of end-repaired and dA-tailed 3.6 kb DNA (SEQ ID NO: 5) was ligated for 60 minutes at room temperature in 300 µL with 150 µL of 35 nM size selection adapter, 15 µL of T4 DNA Ligase (NEB), 60 µL of ligation buffer (50 mM Tris pH8.0, 50 mM MgCl2, 10 mM ATPγS, 32% PEG 8000) and 71 µL of nuclease free water. This is referred to below as the "ligation mixture".

Binding of DNA Ligated to Size Selection Adapter to Beads

50 µL of MagStrep "Type 3" beads (IBA) were washed twice with 150 µL of 50 mM Tris-HCl (pH 8.0 @ 4 C), 150 mM NaCl, 1 mM EDTA. The beads were resuspended in 150 µL of 50 mM Tris-HCl pH8.0 @ 4 C, 20 mM NaCl, and added to the ligation mixture.

The beads were pelleted on a magnetic rack. The supernatant was removed. The beads were washed twice with 150 µL of 50 mM Tris-HCl (pH 8.0 @ 4 C) 150 mM NaCl, 1 mM EDTA. The beads were re-suspended in 150 µL of 50 mM Tris-HCl pH8.0 @ 4 C, 20 mM NaCl.

Movement of Helicase

The sample was split into twelve 10 µL fractions. The beads were pelleted and the buffer removed. Fuel was added to initiate helicase movement by re-suspending the beads in 5 µL of ATP buffer (1 mM MgCl2, 10 mM ATP, 150 mM NaCl and 50 mM Tris pH8.0). The sample was left to incubate with the ATP buffer for 15, 30, 60, 75, 90, 120, 300, 600, 900, 1800 or 3600 seconds. At the end of the defined time period, helicase movement was stopped by pelleting the beads and adding 5 µL of 0.5M EDTA (SIGMA) to the sample and mixed thoroughly. The beads were pelleted and the 10 µL supernatant was removed to a separate tube. A 0 second sample was made in which no ATP buffer was added to the sample, instead 10 of 0.5 M EDTA was added.

Determining Time Point at which 3.6 kb DNA was Released from the Beads

2 µL of purple loading dye (NEB) was added to the supernatant and mixed thoroughly. This is referred to as the 'eluted from beads' sample.

The bead pellet was re-suspended in 10 µL of TBA XT Biotin Elution buffer. Then 2 µL of purple loading dye (NEB) was added to the suspension and mixed thoroughly. This sample is referred to as the 'left on beads' sample.

The samples were loaded onto a 4-20% TBE gel, for 90 minutes at 180 V. Stained in SYBR gold nucleic acid gel stain (Thermofisher) and imaged on the UV gel doc it (GelDoc-It Imaging Systems (UVP)).

Results

The results indicate that the 3.6 kb analyte is released from the bead after a defined time period of 31-60 seconds. This indicates that the helicase is translocating along the DNA at a rate of 60-116 base pairs per second in these buffer conditions at this temperature. When the helicase reaches the end of the strand, the strand is released from the bead. This Example shows that DNA of desirable sizes could be separated from and/or characterised independently from or preferentially to DNA of other sizes using this method; the helicase would reach the end of the differently sized fragments after a different amount of time, and these fractions could be collected separately to collect DNA of different lengths. The helicase could be slowed down or sped up with lower or higher ATP concentrations, to allow a higher degree of separation, or to facilitate faster separation of very long strands.

Some of the 3.6 kb is not released from the bead after 60 seconds, this could indicate that the helicase has encountered some sort of DNA damage on the strand, and has become paused. This indicates that this method could be used for the separation of damaged from un-damaged DNA.

Example 2

This Example describes a method for selectively characterising polynucleotides their lengths using a tagged DNA translocase to select polynucleotides for characterisation. The method used corresponds to the embodiment outlined in FIG. 1.

Materials and Methods

Preparation of the Size Selection Adapter

The size selection adapter comprises a top strand (SEQ ID NO: 1), a bottom strand (SEQ ID NO: 2) and a blocker strand (SEQ ID NO: 6) annealed together at 4.72 µM, 5.66 µM and 5.66 µM respectively in 50 mM HEPES pH 8, 100 mM potassium acetate, 1 mM EDTA from 95° C. to 22° C. at 2° C. per minute. 360 µL of a 4 µM DNA helicase (Dda) containing a strep-SUMO tag (ID4 below), in 50 mM HEPES pH 8, 100 mM potassium acetate. 1 mM EDTA buffer was added to 40 µL of the annealed DNA. The helicase was bound to the size selection adapter for 45 minutes at room temperature, and 5 µL of 8.1 mM Diamide (SIGMA-ALDRICH) was added. The sample was incubated at 35° C. for 60 minutes. 40 µL of 5 M NaCl and 15 µL of nuclease free water were added, and the sample was left for 30 minutes at room temperature. The sample was purified on an HQ10 column. The helicase bound annealed DNA was separated from the unbound DNA. The helicase bound DNA is referred to as the 'size selection adapter'.

31            32

Preparation of Lambda Libraries of Different Sizes

A <1 kb library was prepared using NEB DNA frag-mentase, following the manufacturer's guidelines. Libraries of ~6 kb, ~10 kb and ~20 kb were prepared separately using Covaris G-tube, following the manufacturer's guidelines. A ~48.5 kb library was prepared using un-fragmented lambda DNA. Briefly, the Lambda genomic DNA from NEB (N3013) was diluted to the concentration specified by the manufacturer in nuclease free water. The DNA was heated to 65° C. for 5 minutes and then placed on ice. The DNA was treated following the manufacturer's guidelines to achieve libraries with median lengths previously specified. The DNA was then end repaired and dA tailed using NEBNext Ultra II end repair and dA tailing kit (E7546) following the manufacturer's guidelines. The sample was cleaned using AMPure XP SPRI beads following the manufacturer's guidelines. The libraries were eluted in TE buffer and stored at 4° C.

Preparation of the Mixed Library 138 ng of <1 kb library, 1649 ng of 6 kb library, 2762 ng of 10 kb library, 5565 ng of 20 kb library and 14001 ng of 48.5 kb library were mixed together. This is referred to as the 'mixed DNA library'.

Binding the Adapter to Beads

130 μL of IBA Type 3 beads were washed twice with 200 μL of 50 mM Tris-HCl (pH 8.0 @ 4° C.), 150 mM NaCl, 1 mM EDTA. The size selection adapter was bound to the beads at 4° C. overnight. The beads were washed twice with 300 μL of 50 mM Tris-HCl (pH 8.0 @ 4° C.), 150 mM NaCl, 1 mM EDTA. The beads were pelleted on a magnet.

Binding the Mixed Library to Beads Via the Adapter

The buffer was replaced with 55 μL of the 300 ng/μL mixed DNA library. 10 μL of T4 DNA Ligase (NEB) and 20 μL of ligation buffer (50 mM Tris pH8.0, 25 mM MgCl2, 5 mM ATPγS, 32% PEG 8000 were added before incubating overnight at 4° C.

Movement of Helicase

The sample was split into 5, 20 μL volumes. The beads were bound to the magnet and washed with 120 μL of 10 mM Tris-HCl (pH 8.0 @ 4° C.), 150 mM NaCl, 1 mM EDTA. The beads were re-suspended in 25 μL of 25 mM HEPES pH8.0, 500 mM KCl. To four of the samples 25 μL of 10 mM Tris-HCl (pH 8.0 @ 4° C.), 500 mM NaCl, 20 mM ATP and 2 mM MgCl2 was added. The samples were left for 20, 40, 120 or 240 seconds. 25 μL 0.5 M EDTA was added after the defined time period. The beads were pelleted and washed with 120 μL of 50 mM Tris-HCl (pH 8.0 @ 4° C.), 2 M NaCl, 1 mM EDTA. The beads were pelleted and washed twice with 120 μL of 50 mM Tris-HCl (pH 8.0 @ 4° C.), 150 mM NaCl, 1 mM EDTA.

Addition of Sequencing Adapters

The beads were re-suspended in 20 μL of 10 mM Tris-HCl (pH 8.0 @ 4° C.), 20 mM NaCl. 10 μL of barcode adapter mix (BAM) from Oxford Nanopore sequencing kit EXP- NBD103 and 30 μL of Blunt/TA Ligase Master Mix (NEB) were added, and the samples incubated for 10 minutes at room temperature.

Removal of Remaining DNA from Beads

To remove the remaining DNA from the beads, the helicase was reactivated by adding 60 μL RBF (running buffer with fuel mix) from Oxford Nanopore sequencing kit SQK-LSK108 and incubating the samples for 5 minutes at room temperature. This allowed the helicase bound to the beads to run off the end of the DNAs to which it was bound, and release the DNA.

Sequencing

To clean up the DNS, 60 μL AMPure XP SPRI beads was added and the samples incubated for 10 minutes at room temperature. The sample was washed twice with 120 μL of ABB from Oxford Nanopore sequencing kit SQK-LSK108. The sample was eluted in 21.5 μL of 10 mM Tris-HCl (pH 8.0 @ 4° C.), 20 mM NaCl for 10 minutes. 16 μL of elution buffer (ELB) from Oxford Nanopore sequencing kit SQK-LSK108 was added followed by 37.5 μL of RBF from Oxford Nanopore sequencing kit SQK-LSK108. 75 μL of this sequencing mix was then added to the Oxford Nanopore Minion, using the SpotOn Flowcell Port. The experiment was run at −180 mV and helicase-controlled DNA move-ment was monitored.

Results

The results shown in FIG. 9A indicate that strands with a duration of <5 seconds are depleted when the sample is incubated with ATP for 240 seconds. The results in FIG. 9B indicate that the shorter strands are depleted more with a longer incubation in ATP, whilst the longer strands are not depleted.

Table 1 shows the percentages of strands binned into categories of less than 3000 kilobases, 3000-8000 kilobases, and greater than 8000 kilobases for the initial control sample (0 s incubation) and the libraries prepared from the 120 s and 240 s helicase incubations. The data shows a reduction in strands in the <3000 kb range, and an increase in the strands in 3000-8000 and >8000 ranges, for the libraries prepared from 120 s and 240 s incubation times.

TABLE 1

Figure 9:
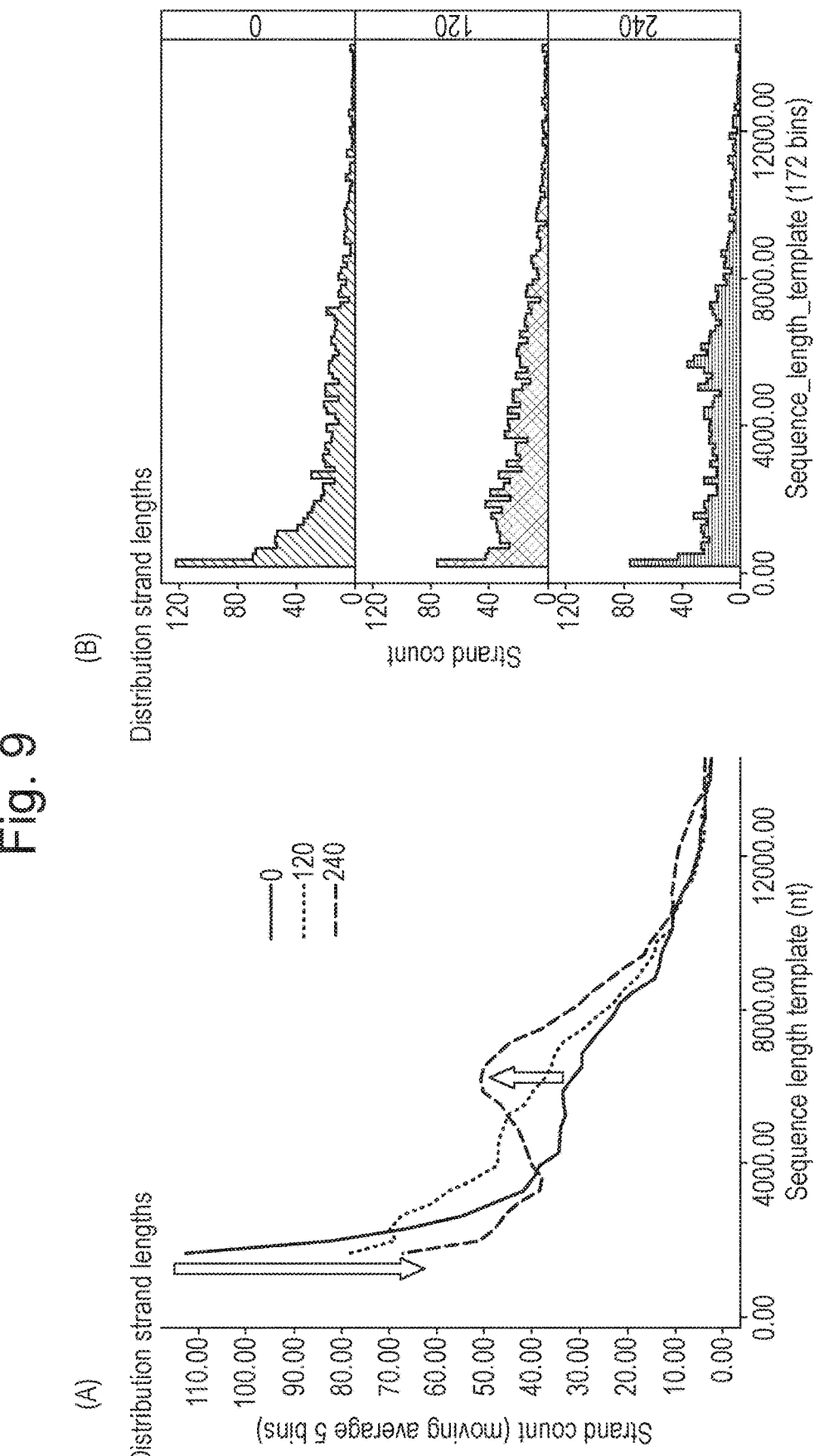
FIG. 9 shows the size distribution of polynucleotides selected from a library of DNA of mixed lengths to which an adapter with an un-stalled helicase had been bound. The size of the polynucleotides was determined by nanopore sequencing. ATP and Mg were added to the library for 120 seconds or 240 seconds prior to stopping the helicase and selecting the DNA strands to which the helicase remained bound.

| Values from FIG. 9 | | | | |
|---|---|---|---|---|
| Incubation time (s) | Number of strands | % <3000 kilobases | % 3000-8000 kilobases | % >8000 kilobases |
| 0 (control) | 1342 | 53.7 | 34.4 | 12.0 |
| 120 | 1357 | 45.2 | 42.4 | 12.4 |
| 240 | 1344 | 35.6 | 48.4 | 16.1 |

The invention claimed is:

1. A method for selecting polynucleotides for characterizing that are at least 1 kb in length, the method comprising:

(i) allowing a plurality of nucleic acid handling enzymes to move along multiple polynucleotides in a sample for a defined time period, wherein the enzymes of the plurality are loaded onto each of the multiple polynucleotides and wherein one or more of the enzymes moves along each of the multiple polynucleotides;

(ii) selecting polynucleotides from step (i) that are at least 1 kb in length based on whether or not the enzymes reach the end of and/or unbind from the polynucleotides in the defined time period;

(iii) physically separating the selected polynucleotides from unselected polynucleotides having a length less than 1 kb prior to contacting the selected polynucleotides with a transmembrane pore in step (iv), wherein the physical separation does not comprise gel electrophoresis; and (iv) characterizing the selected polynucleotides, wherein the characterizing step (iv) comprises (a) contacting the selected polynucleotides with the transmembrane pore.

2. A method according to claim 1, wherein the method comprises an initial step of attaching an adapter to one or both ends of the multiple polynucleotides and then binding the enzyme to the adapter or wherein the method comprises an initial step of attaching an adapter having the enzyme pre-bound thereto to one or both ends of each of the multiple polynucleotides under conditions where the enzyme does not move along the polynucleotides.

3. A method according to claim 1, wherein additional molecules of the enzyme are prevented from binding to the multiple polynucleotides in step (i).

4. A method according to claim 1, wherein the defined time period is started by initiating movement of the enzyme by adding a nucleotide that provides energy for the enzyme, a coenzyme and/or a cofactor, and wherein the defined time period is stopped by inhibiting movement of the enzyme.

5. A method according to claim 1, wherein at the start of step (i) only one molecule of the enzyme is bound to each of the multiple polynucleotides; or wherein at the start of step (i) multiple molecules of the enzyme are bound to each of the multiple polynucleotides; or wherein at the start of step (i) no molecules of the enzyme are bound to any of the multiple polynucleotides and the defined time period is started by contacting the multiple polynucleotides with the enzyme.

6. A method according to claim 1, wherein an adapter comprising an end signal is attached to one or both ends of each of the multiple polynucleotides and wherein the end signal is a selection tag, a hidden site for attaching a further polynucleotide, an exposed site for attaching a further polynucleotide or a cap preventing digestion by an exonuclease; and wherein in step (i) the selection tag is displaced, the hidden site is revealed, the exposed site is removed or the cap is removed when a molecule of the enzyme reaches the end of the polynucleotide; and in step (ii) the selection tag, hidden site, exposed site or uncapped end is used to separate the polynucleotides.

7. A method according to claim 1, wherein the multiple polynucleotides are bound to a bead, column or surface via a selection tag and displacement of the selection tag by the enzyme results in the polynucleotide to which the enzyme is no longer attached being released from the bead, column or surface.

8. A method according to claim 1, wherein in step (ii) polynucleotides to which the enzyme remains bound are separated in step (iii) from polynucleotides to which the enzyme is not bound.

9. A method according to claim 1, wherein the selected polynucleotides are longer or shorter than the unselected polynucleotides, or wherein the selected polynucleotides are damaged and the unselected-polynucleotides are undamaged, or the selected polynucleotides are undamaged and the unselected polynucleotides are damaged, or wherein the selected polynucleotides are selectively modified.

10. A method according to claim 9, wherein the damaged polynucleotides are nicked and the undamaged polynucleotides are intact, wherein nicked polynucleotides are separated from intact polynucleotides, and wherein the selected polynucleotides are selectively modified, and the selectively modified polynucleotides are nicked or the selectively modified polynucleotides are intact.

11. A method according to claim 1, wherein: in step (i) the defined time period is started by adding a capture strand which binds to the enzyme to prevent additional molecules of the enzyme binding to the multiple polynucleotides; and in step (ii) polynucleotides to which the enzyme remains bound are separated in step (iii) from polynucleotides to which the enzyme is not bound.

12. A method according to claim 1, wherein an adapter is attached to each of the multiple polynucleotides, wherein a second nucleic acid handling enzyme is attached to the adapter and is stalled on the adapter such that it does not move along the polynucleotide in step (i).

13. A method according to claim 1, wherein step (ii) comprises: binding a hidden or exposed site to an adapter comprising a single stranded leader sequence, wherein a second nucleic acid handling enzyme is attached to the adapter and is stalled on the adapter; and step (iv) comprises bringing the selected polynucleotides into contact with the transmembrane pore.

14. A method according to claim 1, wherein the enzyme is a translocase, a helicase, a polymerase or an exonuclease.

15. A method according to claim 1, wherein the polynucleotides are DNA, RNA and/or DNA/RNA hybrids.

16. A method according to claim 1, wherein the sample comprises one or more groups selected from the group consisting of:

(a) products of a PCR reaction;

(b) a DNA library;

(c) genomic DNA; and (d) products of a endonuclease digestion.

17. A method according to claim 1, further comprising one or more additional steps selected from the group consisting of:

sequencing the selected polynucleotides;

removing primers or adapters from the selected polynucleotides; and genotyping, DNA fingerprinting or profiling using the selected polynucleotides.

18. The method according to claim 1, wherein the characterizing step (iv) further comprises:

(b) applying a potential difference across the transmembrane pore; and (c) taking one or more measurements which are indicative of one or more characteristics of a polynucleotide moving with respect to the transmembrane pore and thereby characterising the polynucleotide.

19. The method according to claim 1, wherein the characterizing step (iv) further comprises:

(b) applying a potential difference across the transmembrane pore; and (c) taking one or more measurements which are indicative of one or more characteristics of a polynucleotide moving with respect to the transmembrane pore and thereby characterising the polynucleotide, wherein the method further comprises measuring the current passing through the transmembrane pore as the polynucleotide moves with respect to the transmembrane pore.

20. The method according to claim 1, wherein the selecting comprises selecting polynucleotides at least 10 kb in length.

21. The method according to claim 1, wherein the selecting comprises selecting polynucleotides at least 50 kb in length.

22. The method of claim 4, wherein the defined time period is stopped by inhibiting movement of the enzyme by (a) removing a nucleotide that provides energy for the enzyme, a coenzyme and/or a cofactor; (b) adding an enzyme inhibitor; (c) changing the pH, temperature or salt concentration; and/or (d) denaturing the enzyme.

23. The method according to claim 8, wherein the defined time period is stopped by flushing the bead, column, or surface.

24. The method according to claim 8, wherein polynucleotides not bound to the bead, column or surface are removed or eluted by washing.

* * * * *